US012016844B2

(12) United States Patent
Bartsich

(10) Patent No.: US 12,016,844 B2
(45) Date of Patent: *Jun. 25, 2024

(54) MAMMARY TUMOR VIRUS SUPPRESSION

(71) Applicant: VIRAGO VAX INC., New York, NY (US)

(72) Inventor: Sophie Bartsich, New York, NY (US)

(73) Assignee: VIRAGO VAX INC., New York, NY (US)

(*) Notice: Subject to any disclaimer, the term of this patent is extended or adjusted under 35 U.S.C. 154(b) by 6 days.

This patent is subject to a terminal disclaimer.

(21) Appl. No.: 16/920,089

(22) Filed: Jul. 2, 2020

(65) Prior Publication Data

US 2021/0000800 A1  Jan. 7, 2021

Related U.S. Application Data

(63) Continuation-in-part of application No. 16/460,295, filed on Jul. 2, 2019.

(60) Provisional application No. 62/934,858, filed on Nov. 13, 2019.

(51) Int. Cl.
| | | |
|---|---|---|
| A61K 39/00 | (2006.01) | |
| A61K 31/427 | (2006.01) | |
| A61K 31/4418 | (2006.01) | |
| A61K 39/21 | (2006.01) | |
| C07K 14/005 | (2006.01) | |
| C12N 7/00 | (2006.01) | |
| G01N 33/574 | (2006.01) | |

(52) U.S. Cl.
CPC ........ A61K 31/427 (2013.01); A61K 31/4418 (2013.01); A61K 39/21 (2013.01); C07K 14/005 (2013.01); C12N 7/00 (2013.01); G01N 33/57415 (2013.01); C12N 2740/12022 (2013.01); C12N 2740/12034 (2013.01)

(58) Field of Classification Search
None
See application file for complete search history.

(56) References Cited

U.S. PATENT DOCUMENTS

| | | |
|---|---|---|
| 6,258,932 B1 | 1/2001 | Vahlne |
| 6,670,466 B1 | 1/2003 | Garry |
| 9,383,367 B1 | 7/2016 | Liu et al. |
| 2007/0281911 A1 | 12/2007 | Cihlar et al. |
| 2009/0269364 A1 | 10/2009 | Zielinski et al. |
| 2012/0135950 A1 | 5/2012 | Kaplan et al. |
| 2014/0271687 A1 | 9/2014 | Kovesdi et al. |
| 2015/0174237 A1 | 6/2015 | Mond et al. |
| 2019/0343938 A1 | 11/2019 | Bartsich |
| 2021/0000800 A1 | 1/2021 | Bartsich |

FOREIGN PATENT DOCUMENTS

| | | |
|---|---|---|
| EP | 3993873 | 5/2022 |
| WO | 9951268 | 10/1999 |
| WO | 1999051267 A1 | 10/1999 |
| WO | 2017147078 A1 | 8/2017 |
| WO | 2021003421 | 7/2021 |

OTHER PUBLICATIONS

Bryson et al., Vaccine vol. 35, pp. 5842-5849 (Year: 2017).*
Denner et al. (Virus Research vol. 208, pp. 39-43 (Year: 2008).*
Tang MW, Shafer RW. Drugs. Jun. 18, 2012;72(9):e1-25. (Year: 2012).*
Agut H, [translated title—Antiviral chemotherapy: mechanisms of action, evaluation of activity, resistance and future developments]. Pathol Biol (Paris). Oct. 1993;41(8 Pt 2):770-6. French. Abstract only (Year: 1993).*
Hillier, Sharon L et al., JAIDS Journal of Acquired Immune Deficiency Syndromes: May 1, 2005—vol. 39—Issue 1—p. 1-8 doi: 10.1097/01.qai.0000159671.25950.74 (Year: 2005).*
Levine P. Increasing evidence for a human breast carcinoma virus with geographic differences. Cancer, 2004. 101: 721-726.
Levine P. Increased detection of breast cancer virus sequences in inflammatory breast cancer. Adv Tumor Virol. 2009. 1: 3-7.
Links J. The Growth Accelerating Effect of Bittner Virus in Monolayers of Baby Mouse Kidney Cells. J. Gen Virol, 1969. 5:547-550.
Litvinov S. Expression of proteins immunologically related to murine mammary tumor virus (MMTV) core proteins in cells of breast cancer continuous cell lines MCF7, T47D, MDA-MB231 and cells from human milk. Acta Virol. 1989. 33:137-142.
Liu B. Identification of a proviral structure in human breast cancer. Cancer Res, 2001. 61: 1754-1759.
Lloyd R. Murine mammary tumor virus related antigen in human male mammary carcinoma. Cancer, 1983. 51:654-661.
Lower R. The pathogenic potential of endogenous retroviruses: facts and fantasies. Trends in Microbiology, 1999. 7: 9, 350-356.
Luo T. Study of mouse mammary tumor virus-like gene sequences expressing breast tumors of Chinese women. Sichuan Da Xue Xue Bao Yi Xue Ban, 2006. 37: 844-846.
Lynch H. Is cancer communicable? Med Hypotheses, 1984. 14: 181-198.
MacMahon B. Etiology of human breast cancer: a review. J Natl Cancer Inst. 1973. 50:21-42.
Mager D. Herv-H endogenous retroviruses: presence in the new world branch but amplification in the old world primate lineage. Virology, 1995. 213: 395-404.

(Continued)

Primary Examiner — Shanon A. Foley
Assistant Examiner — Myron G Hill
(74) Attorney, Agent, or Firm — Grogan, Tuccillo & Vanderleeden, LLP

(57) ABSTRACT

Disclosed are methods of treating a patient exposed to MTV. Also disclosed is a purified cDNA encoding an MTV transition protein peptide chain. Also disclosed is a vaccine containing an MTV transition protein. A further version of the invention is a vaccine comprising MTV polypeptides coupled to a carrier protein. MTV may be treated by providing an MTV vaccine with an MTV transition protein; and, administering said vaccine. In further instances, the MTV vaccine is administered with an antiretroviral medication.

16 Claims, 3 Drawing Sheets

Figure 1:

Specification includes a Sequence Listing.

(56) References Cited

OTHER PUBLICATIONS

Mager D. Novel Mouse Type D Endogenous Proviruses and Elements Share Long Terminal Repeat and Internal Sequences. J Virology, 2000. 74: 16, 7221-7229.

Mant C. A human murine mammary tumor virus-like agents are genetically distinct from endogenous retroviruses and not detectable in breast cancer cell lines of biopsies. Virology, 2004. 318: 393-403.

Marchetti A. Host Genetic Background Effect o the Frequency of Mouse Mammary Tumor Virus-Induced Rearrangements of the int-1 and int-2 Loci in Mouse Mammary Tumors. J Virology, 1991. 65: 8, 4550-4554.

Marrack P. A maternally inherited superantigen encoded by a mammary tumour virus. Nature, 1991. 349:524-525.

Melana S. Search for mouse mammary tumor virus-like env sequences in cancer and normal breast from the same individuals. Clin Cancer Res, 2001. 7: 283-284.

Melana S. Characterization of viral particles isolated from primary cultures of human breast cancer cells. Cancer Res, 2007. 67:8960-8965.

Moore D. Search for a human breast cancer virus. Nature, 1971. 229: 611-615.

Mueller-Lantzsch N. Human Endogenous Retroviral Element K10 (KERV-K10) Encodes a Full-Length Gag Homologous 73-kDa Protein and a Functional Protease. AIDS Research and Human Retroviruses, 1993. 9: 4, 343-350.

Nusse R. The int genes in mammary tumorigenesis and in normal development. TIG, 1988. 4: 10, 291-295.

Ono M. Stimulation of Expression of the Human Endogenous Retrovirus Genome by Female Steroid Hormones in Human Breast Cancer Cell Line T47D. Journal of Virology, 1987. 61:2059-2062.

Paces J. Herv: database of human endogenous retroviruses. Nucleic Acids Research, 2002. 30:1, 205-206.

Palmarini M. The Exogenous Form of Jaagsiekte Retrovirus is Specifically Associated with a Contagious Lung Cancer of Sheep. J of Virology, 1996. 70: 3, 1618-1623.

Peters G. Tumorigenesis by Mouse Mammary Tumor Virus: Evidence for a Common Region for Provirus Integration in Mammary Tumors. Cell, 1983. 33:36-377.

Pogo B. Detection of mammary tumor virus env gene-like sequences in human breast cancer. Cancer Res, 1995. 55:5173-5179.

Pogo B. Sequences homologous to the MMTV env gene in human breast carcinoma correlate with overexpression of laminin receptor. Clin Cancer Res. 1999. 5: 2108-2111.

Prak E. Mobile Elements and the Human Genome. Nature Reviews Genetics, 2000. 1: 134-144.

Reus K. HERV-K (OLD): Ancestor Sequences of the Human Endogenous Retrovirus Family HERV-K (HNL-2). J Virology, 2001. 75: 19, 8917-8926.

Reuss F. cDNA Sequence and Genomic Characterization of Intracisternal A-Particle—Related Retroviral Elements Containing an Envelope Gene. J Virology, 1991. 65: 11, 5702-5709.

Rous P. A sarcoma of the fowl transmissible by an agent separable from the tumor cells. J Exp Med, 1911. 13: 397.

Russ J. Identical cancers in husband and wife. Surg Gynecol Obstet, 1980. 150: 664-666.

Salmons B. Production of mouse mammary tumor virus upon transfection of a recombinant proviral DNA into cultured cells. Virology, 1985. 144: 101-114.

Shackleford G. Mouse mammary tumor virus infection accelerates mammary carcinogenesis in Wnt-1 transgenic mice by insertional activation of int-1/Fgf-3 and hst/ Fgf-4. Proc Natl Acad Sci USA, 1993. 90:740-744.

Smit A. Interspersed repeats and other mementos of transposable elements in mammalian genomes. Current Opinion in Genetics & Development, 1999. 9: 657-663.

Stewart A. Identification of Human Homologues of the Mouse Mammary Tumor Virus Receptor. Archives of Virology, 2002. 147:577-581.

Stewart S. Burkitt's tumour: tissue culture, cytogenetic and virus studies. J Nat Cancer Inst, 1964. 34: 319.

Stewart T. Breast Cancer Incidence Highest in the Range of One Species of House Mouse, Mus Domesticus. British Journal of Cancer, 2000. 82:446-451.

Sumidaie A. Particles with Properties of Retroviruses in Monocytes from Patients with Breast Cancer. The Lancet, 1988. 5-9.

Szabo S. Of Mice, Cats and Men: Is human breast cancer a zoonosis? Microsc Res Tech, 2005. 68:197-208.

Tchenio T. Defective Retroviruses Can Disperse in the Human Genome by Intracellular Transposition. Journal of Virology, 1991. 65:2113-2118 Time, Cancer Virus, Mar. 18, 1946.

Tonjes R. Characterization of Human Endogenous Retrovirus Type K Virus-like Particles Generated from Recombinant Baculoviruses. Virology, 1997. 233: 280-291.

Tristem M. Identification and Characterization of Novel Human Endogenous Retrovirus Families by Pylogenetic Screening of the Human Genome Mapping Project Database. J Virology, 2000. 74:8, 3715-3730.

Tsubura A. Intervention of T-cells in transportation of mouse mammary tumor virus to mammary gland cells in vivo. Canc. Res, 1988 48:6555-59.

Turner G. Insertional polymorphisms of full-length endogenous retroviruses in human. Current Biology, 2001. 11:1531-1535.

Wang Y. Detection of mammary tumor virus env gene-like sequences in human breast cancer. Cancer Res, 1995. 55:5173-5179.

Wang Y. Detection of MMTVlike LTR and LTR-env gene sequences in human breast cancer. Int J Oncology, 2001. 18:1041-1044.

Wang Y. Presence of MMTV-like env gene sequences in gestational breast cancer. Med Oncol, 2003. 20: 233-236.

Wang Y. A mouse mammary tumor virus-like long terminal repeat superantigen in human breast cancer. Cancer Res, 2004. 64: 4105-4111.

Westley B. The human genome contains multiple sequences of varying homology to mouse mammary tumour virus DNA. Gene, 1984. 28:221-227.

Witkin A. Antigens and antibodies cross-reactive to the murine mammary tumor virus in human breast cyst fluids. J Clin Invest, 1981. 67:216-222.

Witt A. The mouse mammary tumor virus-like sequence is not detectable in breast cancer tissue of Austrian patients. Oncol Rep, 2003. 10: 1025-1029.

Wright D. Burkitt's tumor and childhood lymphosarcoma. Clin Ped. 1967. 6: 116.

Xu L. Does a betaretrovirus infection trigger primary biliary cirrhosis? Proc Natl Acad Sci, 2003. 100: 8454-8459.

Yang M. Presence of a mouse mammary tumor virus MMTV-related antigen in human breast carcinoma cells and its absence from normal epithelial cells. J Natl Cancer Inst, 1978. 61:1205-1207.

Zammarchi F. MMTV-like sequences in human breast cancer: a fluorescent PCR/laser microdissection approach. Journal of Pathology, 2006. 209:436-444.

Zapata-Benavides P. Mouse mammary tumor virus-like gene sequences in breast cancer samples of Mexican women. Intervirology, 2007. 50:402-407.

Alibek K, Kakpenova A, Mussabekova A, Sypabekova M, Karatayeva N. Role of viruses in the development of breast cancer. Infect Agent Cancer 2013;8:32.

Mirzaei H, Faghihloo E. Viruses as key modulators of the TGF-β pathway; a double-edged sword involved in cancer. Rev Med Virol 2018;28(2).

Reza MA, Reza MH, Mahdiyeh L, Mehdi F, Hamid ZN. Evaluation Frequency of Merkel Cell Polyoma, Epstein-Barr and Mouse Mammary Tumor Viruses in Patients with Breast Cancer in Kerman, Southeast of Iran. Asian Pac J Cancer Prev 2015;16(16):7351-7.

Carolis S, Pellegrini A, Santini D, et al. Liquid biopsy in the diagnosis of HPV DNA in breast lesions. Future Microbiol 2018;13:187-194.

Franklin GC, Chretien S, Hanson IM, Rochefort H, May FE, Westley BR. Expression of human sequences related to those of mouse mammary tumor virus. J Virol 1988;62(4):1203-10.

Etkind PR, Alexandre FR, Wiernik PH. Mouse mammary tumor virus (MMTV)-like DNA sequences in the breast tumors of father, mother, and daughter. Infect Agent Cancer 2008;3(2).

(56) References Cited

OTHER PUBLICATIONS

Szakacs JG, Moscinski LC. Sequence homology of deoxyribonucleic acid to mouse mammary tumor virus genome in human breast tumors. Ann Clin Lab Sci 1991;21(6):402-12.
Naushad W, Bin Rahat T, Gomez MK, Ashiq MT, Younas M, Sadia H. Detection and identification of mouse mammary tumor virus-like DNA sequences in blood and breast tissues of breast cancer Tumour Biol 2014;35(8):8077-86.
Wang F, Hou J, Shen Q, et al. Mouse mammary tumor virus-like virus infection and the risk of human breast cancer. a meta-analysis. Am J Transl Res 2014;6(3):248-66.
May FE, Westley BR, Rochefort H, Buetti E, Diggelmann H. Mouse mammary tumour virus related sequences are present in human DNA. Nucleic Acids Res 1983;11(12):4127-39.
Kincaid RP, Panicker NG, Lozano MM, Sullivan CS, Dudley JP, Mustafa F. MMTV does not encode viral microRNAs but alters the levels of cancer-associated host microRNAs. Virology 2018;513:180-187.
Day NK, Witkin SS, Sarkar NH, et al. Geographic and family studies of immunological responses to antigens of the murine mammary tumor virus in sera of patients with breast cancer. Trans Assoc Am Physicians 1980;93:123-9.
Lawson JS, Glenn WK, Whitaker NJ. Human Papilloma Viruses and Breast Cancer—Assessment of Causality. Front Oncol 2016;6:207.
Xue XY, Majerciak V, Uberoi A, et al. The full transcription map of mouse papillomavirus type 1 (MmuPV1) in mouse wart tissues. PLoS Pathog 2017;13(11):e1006715.
Froissart R, Wilke CO, Montville R, Remold SK, Chao L, Turner PE. Co-infection weakens selection against epistatic mutations in RNA viruses. Genetics. 2004;168(1):9-19.
Crépin M, Lidereau R, Chermann JC, et al. Sequences related to mouse mammary tumor virus genome in tumor cells and lymphocytes from patients with breast cancer. Biochem Biophys Res Commun 1984;118(1):324-31.
Lopez DM, Parks WP, Silverman MA, Distasio JA. Lymphoproliferative responses to mouse mammary tumor virus in lymphocyte subsets of breast cancer patients. J Natl Cancer Inst 1981;67(2):353-8.
Johal H, Ford C, Glenn W, Heads J, Lawson J, Rawlinson W. Mouse mammary tumor like virus sequences in breast milk from healthy lactating women. Breast Cancer Res Treat 2011;129(1):149-55.
Finn OJ, Rammensee HG. Is It Possible to Develop Cancer Vaccines to Neoantigens, What Are the Major Challenges, and How Can These Be Overcome? Neoantigens: Nothing New in Spite of the Name. Cold Spring Harb Perspect Biol 2017;pii: a028829.
Lawson JS, Glenn WK, Salmons B, Ye Y, Heng B, Moody P, Johal H, Rawlinson WD, Delprado W, Lutze-Mann L, Whitaker NJ. Mouse mammary tumor virus-like sequences in human breast cancer. Cancer Res 2010;70(9):3576-85.
Crepin M, Lidereau R, Chermann JC, Pouillart P, Magdamenat H, Montagnier L. Sequences related to mouse mammary tumor virus genome in tumor cells and lymphocytesfrom patients with breast cancer. Biochem Biophys Res Commun 1984;118(1):324-31.
Deligdisch L, Marin T, Lee AT, et al. Human mammary tumor virus (HMTV) in endometrial carcinoma. Int J Gynecol Cancer 2013;23(8):1423-8.
Svec J, Hlavay E, Matoska J, Thurzo V. Hormone-responsive genes of the mouse mammary tumor virus. Czech Med 1979;2(4):198-212.
Pogo BG, Holland JF, Levine PH. Human mammary tumor virus in inflammatory breast cancer. Cancer 2010;116(11 Suppl):2741-4.
Perzova R, Abbott L, Benz P, et al. Is MMTV associated with human breast cancer? Maybe, but probably not. Virol J 2017;14(1):196.
Duesberg PH, Blair PB. Isolation of the nucleic acid of mouse mammary tumor virus (MTV). Proc Natl Acad Sci U S A 1966;55(6):1490-7.
Vinner L, Mourier T, Friis-Nielsen J, et al. Investigation of Human Cancers for Retrovirus by Low-Stringency Target Enrichment and High-Throughput Sequencing. Sci Rep 2015;5:13201.
Bozorgi A, Khazaei M, Khazaei MR. New Findings on Breast Cancer Stem Cells: A Review. J Breast Cancer 2015;18(4):303-12.
Nusse et al., "Localization of a Gene for Expression of Mouse Mammary Tumor Virus Antigens in the GR/Mtv2-Mouse Strain", J. Exp. Med, The Rockefeller University Press, vol. 152, Sep. 1980, pp. 712-719.
International Search Report dated Nov. 19, 2019 in corresponding PCT Application No. PCT/US2019/40361.
Wang Y, Holland JF, Bleiweiss IJ, et al. Detection of mammary tumor virus env gene-like sequences in human breast cancer. Cancer Res 1995;55(22):5173-9.
Wei WZ, Gill RF, Wang H. Mouse mammary tumor virus associated antigens and superantigens—immuno-molecular correlates of neoplastic progression. Semin Cancer Biol 1993;4(3):205-13.
Weiss, RA. Retrovirus classification and cell interactions. J Antimicrob Chemother 1996;37. Suppl B:1-11. Review.
Bell T. Isolation of a reovirus from a case of Burkitt's lymphoma. Brit Med J, 1964. 1: 1212.
Andersson A. Expression of human endogenous retrovirus ERV3 (HERV-R) mRNA in normal and neoplastic tissues. Int J Onc, 1998. 12: 309-313.
Benit L. Identification, Phylogeny, and Evolution of Retroviral Elements Based on Their Envelope Genes. J Virology, 2001. 75: 23, 11709-11719.
Bera T. Defective Retrovirus Insertion Activates c-Ha-ras Proto-oncogene in an MNU-Induced Rat Mammary Carcinoma. Biochem Biophy Res Comm, 1998. 248: 835-840.
Berkhout B. Identification of an Active Reverse Transcriptase Enzyme Encoded by a Human Endogenous HERV-K Retrovirus. J Virology, 1999. 73: 3, 2365-2375.
Bindra A. Search for DNA of exogenous mouse mammary tumor virus-related virus in human breast cancer samples. J Gen Virol, 2007. 88: 1806-1809.
Bittner J. Some Possible effects of nursing on the mammary gland tumor incidence in mice. Science, Aug. 14, 1936. 84: 162.
Bittner J. The Milk-Influence of Breast Tumors in Mice. Science, May 1, 1942. 95:462-463.
Blair P. Neutralization of the mouse mammary tumor virus by rabbit antisera against C3Hf tissue. Cancer Res, 1963. 23: 381.
Bock M. Endogenous retroviruses and the human germline. Current Opinions in Genetics & Development, 2000. 10: 651-655.
Day N. Antibodies reactive with murine mammary tumor virus in sera of patients with breast cancer: Geographic and family studies. Proc Natl Acad Sci USA, 1981. 78:2483-2487.
Dion A. A human protein related to the major envelope protein of murine mammary tumor virus: identification and characterization. Proc Natl Acad Sci USA. 1980. 77: 1301-1305.
Omochowski L. The milk agent in the origin of mammary tumors in mice. Adv Cancer Res. 1953. 1:103.
Epstein M. Morphological and biological studies on a virus in cultured lymphoblasts from Burkitt's lymphoma. J Exp Med. 1965. 121:761.
Ekbom A. Breast-feeding and breast cancer in the offspring. British J. Cancer, 1993. 67: 2375-2382.
Etkind P. Mouse mammary tumor virus-like ENV gene sequences in human breast tumors and in a lymphoma of a breast cancer patient. Clin Can Res 2000. 6: 1273-78.
Etkind P. Clonal isolation of different strains of mouse mammary tumor virus-like DNA sequences from both the breast tumors and non-Hodgkin's lymphomas of individual patients diagnosed with both malignancies. Clin Cancer Res 2004. 10: 5656-5664.
Faedo M. Mouse mammary tumor-like virus is associated with p53 nuclear accumulation and progesterone receptor positivity but not estrogen positivity in human female breast cancer. Clin Cancer Res. 2004. 10: 4417-4419.
Fennelly J. Co-amplification of tail-to-tail copies of MuRVY and APE retroviral genomes on the Mus musculus Y Chromosome. Mammalian Genome, 1996, 7: 31-36.
Fernandez-Cobo M. Transcription profiles of non-immortalized breast cancer cells. Biomed Central Cancer, 2006. 6: 99-100.
Ford C. Mouse mammary tumor virus-like gene sequences in breast tumors of Australian and Vietnamese women. Clin Cancer Res, 2003. 9: 1118-1120.

(56) References Cited

OTHER PUBLICATIONS

Ford C. MMTV virus-like RNA transcripts and DNA are found in affected cells of human breast cancer. Clin Cancer Res. 2004. 10: 7284-7289.
Franklin G. Expression of Human Sequences Related to Those of Mouse Mammary Tumor Virus. Journal of Virology, 1988. 62:1203-1210.
Friedman G. Spousal concordance for cancer incidence. A cohort study. Cancer, 2000. 86: 2413-2419.
Fukuoka H. No association of mouse mammary tumor virus-related retrovirus with Japanese cases of breast cancer. J Med Virol. 2008. 80: 1447-1451.
Golovkina T. Coexpression of Exogenous and Endogenous Mouse Mammary Tumor Virus RNA In Vivo Results in Viral Recombination and Broadens the Virus Host Range. Journal of Virology, 1994. 68:5019-5026.
Golovkina, T. A novel membrane protein is a mouse mammary tumor virus receptor. J. Virol. 1998. 72:3066-71.
Gotlieb-Stematsky T. Increased tumor formation by polyoma virus in the presence of non-oncogenic viruses. Nature, 1966. 212: 421.
Gray D. Activation of int-1 and int-2 Loci in GRf Mammary Tumors. Virology, 1986. 154: 271-278.
Griffiths D. Endogenous retroviruses in the human genome sequence. Genome Biology, 2001. 2: 6, 1017.1-1017.5.
Hachana M. Prevalence and characteristics of the MMTV-like associated breast carcinomas in Tunisia. Cancer Lett. 2008. 271: 222-230.
Held W. Reverse Transcriptase-dependent and -independent Phases of Infection with Mouse Mammary Tumor Virus: Implications for Superantigen Function. J Exp Med, 1994. 180:2347-2351.
Heller J. Research on cancer viruses. Public Health Rep. 1960. 75:501.
Howard D. Isolation of a series of novel variants of murine mammary tumor viruses with broadened host range. Int J. Cancer, 1980. 25:647-654.
Hughes J. Evidence for genomic rearrangements mediated by human endogenous retroviruses during primate evolution. Nature Genetics, 2001. 29: 487-489.
Imai S. Distribution of Mouse Mammary Tumor Virus in Asian Wild Mice. Journal of Virology, 1994. 68:3437-3442.
Identity crisis. Nature, 2009. 457: 935-936, Indik S. Mouse mammary tumor virus infects human cells. Cancer Res, 2005. 65: 6651-6659.
Indik S. A novel, mouse mammary tumor virus encoded protein with Rev-like properties. Virology, 2005. 337: 1-6.
Indik S. Rapid spread of mouse mammary tumor virus in cultured human breast cells. Retrovirology, 2007. 4: 73.
Karlsson H. Retroviral RNA identified in the cerebrospinal fluids of brains of individuals with schizophrenia. PNAS, 2001. 98: 8, 4634-4639.
Katz E. MMTV env encodes an ITAM responsible for transformation of mammary epithelial cells in three-dimensional culture. J Exp Med, 2005. 201: 431-439.
Kidd J. The enduring partnership of a neoplastic virus and carcinoma cells. Continued increase of virus in the V2 carcinoma during propagation in virus immune hosts. J Exp Med. 1942. 75:7.
Lawson J. From Bittner to Barr: a viral, diet and hormone breast cancer aetiology hypothesis. Breast Cancer Res, 2001. 3:81-85.
Leib C. Endogenous Retroviral Elements in Human DNA. Cancer research (Supp), 1990. 50:5636-5642.
Levine P. Increased incidence of mouse mammary tumor virus-related antigen in Tunisian patients with breast cancer. Int. J. Cancer, 1984. 3:305-308.
Al Moustafa AE, Al-Antary N, Aboulkassim T, Akil N, Batist G, Yasmeen A. Co-prevalence of Epstein-Barr virus and high-risk human papillomaviruses in Syrian women with breast cancer. Hum Vaccin Immunother 2016;12(7):1936-9.
Salmons B, Lawson JS, Günzburg WH. Recent developments linking retroviruses to human breast cancer: infectious agent, enemy within or both? J Gen Virol 2014;95(Pt 12):2589-93.

Astori M, Karapetian O. Immunization with a mouse mammary tumour virus envelope protein epitope protects against tumour formation without inhibition of the virus infection. J Gen Virol 1997;78(Pt 8):1935-9.
Atique S, Hsieh Chen, Hsiao RT, et al. Viral warts (Human Papilloma Virus) as a potential risk for breast cancer among young females. Comput Methods Programs Biomed 2017;144:203-207.
San TH, Fujisawa M, Fushimi S, et al. Low prevalence of human mammary tumor virus (HMTV) in breast cancer patients from Myanmar. Infect Agent Cancer 2017;12:20.
Bae JM, Kim EH. Human papillomavirus infection and risk of breast cancer: a meta-analysis of case-control studies. Infect Agent Cancer 2016;11:14.
Ballard AJ. Epstein-Barr virus infection is equally distributed across the invasive ductal and invasive lobular forms of breast cancer. Pathol Res Pract 2015;211(12):1003-5.
Baltzell KA, Shen HM, Krishnamurthy S, Sison JD, Nuovo GJ, Buehring GC. Bovine leukemia virus linked to breast cancer but not coinfection with human papillomavirus: case-control study of women in Texas. Cancer 2018;124(7):1342-1349.
Bindra A, Muradrasoli S, Kisekka R, Nordgren H, Wärnberg F, Blomberg J. Search for DNA of exogenous mouse mammary tumor virus-related virus in human breast cancer samples. J Gen Virol 2007;88(Pt 6):1806-9.
Stewart TH, Sage RD, Stewart AF, Cameron DW. Breast cancer incidence highest in the range of one species of house mouse, mus domesticus. Br J Cancer 2000;82(2):446-51.
Szabo S, Haislip AM, Traina-Dorge V, et al. Human, rhesus macaque, and feline sequences highly similar to mouse mammary tumor virus sequences. Microsc Res Tech 2005;68(3-4):209-21.
Buehring GC, Shen H, Schwartz DA, Lawson JS. Bovine leukemia virus linked to breast cancer in Australian women and identified before breast cancer development. Plos One 2017;12(6):e0179367.
Callahan R, Mudunur U, Bargo S, et al. Genes affected by mouse mammary tumor virus (MMTV) proviral insertions in mouse mammary tumors are deregulated or mutated in primary human mammary tumors. Oncotarget 2012;3(11):1320-34.
Cedro-tanda A, Cordova-Solis A, Juarez-Cedillo T, et al. Prevalence of HMTV in breast carcinomas and unaffected tissue from Mexican women. BMC Cancer 2014;14:942.
Chouchane L, Boussen H, Sastry KS. Breast cancer in Arab populations: molecular characteristics and disease management implications. Lancet Oncol 2013;14(10):e417-24.
Coghill AE, Engels EA, Schymura MJ, et al. Risk of breast, prostate, and colorectal cancer diagnoses among HIV-infected individuals in the United States. J Natl Cancer Inst 20181;110(9):959-966.
Corbex M, Bouzbid S, Traverse-Glehen A, et al. Prevalence of papillomaviruses, polyomaviruses, and herpesviruses in triple-negative and inflammatory breast tumors from algeria compared with other types of breast cancer tumors. Plos One 2014;9(12):e114559.
De Vries RD, de Swart RL. Measles immune suppression: functional impairment or numbers game? PLoS Pathog 2014;10(12):e1004482.
Dion AS, Girardi AJ, Williams CC, Pomenti AA. Serologic responses to murine mammary tumor virus (MuMTV) in MuMTV-exposed laboratory personnel. J Natl Cancer Inst 1986;76(4):611-9.
Dudley JP, Golovkina TV, Ross SR. Lessons learned from mouse mammary tumor virus in animal models. ILAR J 2016;57(1):12-23.
Tomana M, Kajdos AH, Niedermeier W, Durkin WJ, Mestecky J. Antibodies to mouse mammary tumor virus-related antigen in sera of patients with breast carcinoma. Cancer 1981;47(11):2696-703.
Faschinger A, Rouault F, Sollner J, Lukas A, Salmons B, Günzburg WH, Indik S. Mouse mammary tumor virus integration site selection in human and mouse genomes. J Virol 2008;82(3):1360-7.
Ford CE, Faedo M, Rawlinson WD. Mouse mammary tumor virus-like RNA transcripts and DNA are found in affected cells of human breast cancer. Clin Cancer Res 2004;10(21):7284-9.
Ford CE, Tran D, Deng Y, Ta VT, Rawlinson WD, Lawson JS. Mouse mammary tumor virus-like gene sequences in breast tumors of Australian and Vietnamese women. Clin Cancer Res 2003;9(3):1118-20.

(56) References Cited

OTHER PUBLICATIONS

Glenn WK, Heng B, Delprado W, Lacopetta B, Whitaker NJ, Lawson JS. Epstein-Barr virus, human papillomavirus and mouse mammary tumour virus as multiple viruses in breast cancer. Plos One 2012;7(11):e48788.
Hsu WL, Lin HY, Chiou SS, Chang CC, et al. House mammary tumor virus-like nucleotide sequences in canine and feline mammary tumors. J Clin Microbiol 2010;48(12):4354-62.
Johal H, Faedo M, Faltas J, et al. DNA of mouse mammary tumor virus-like virus is present in human tumors influenced by hormones. J Med Virol 2010;82(6):1044-50.
Kar SP, Beesley J, Amin Al Olama A, et al. Genome-wide meta-analyses of breast, ovarian, and prostate cancer association studies identify multiple new susceptibility loci shared by at least two cancer types. Cancer Discov 2016;6 (9):1052-67.
Khan NA, Castillo A, Koriyama C, et al. Human papillomavirus detected in female breast carcinomas in Japan. Br J Cancer 2008;99(3):408-14.
Labrecque LG, Barnes DM, Fentiman IS, Griffin BE. Epstein-Barr virus in epithelial cell tumors: a breast cancer study. Cancer Res 1995;55(1):39-45.
Latif N, Rana F, Guthrie T. Breast cancer and HIV in the era of highly active antiretroviral therapy: two case reports and review of the literature. Breast j 2011;17(1):87-92.
Laumbacher B, Fellerhoff B, Herzberger B, et al. Do dogs harbour risk factors for human breast cancer? Med Hypotheses 2006;67(1):21-6. Epub Mar. 3, 2006.
Lawson JS, Mazzanti C, Civita P, et al. Association of mouse mammary tumor virus with human breast cancer: histology, immunohistochemistry and polymerase chain reaction analyses. Front Oncol 2018;8:141.
Lawson JS, Salmons B, Glenn WK. Oncogenic viruses and breast cancer: Mouse Mammary Tumor Virus (MMTV), Bovine Leukemia Virus (BLV), Human Papilloma Virus (HPV), and Epstein-Barr Virus (EBV). Front Oncol 2018;8:1.
Lawson JS, Glenn WK. Multiple oncogenic viruses are present in human breast tissues before development of virus associated breast cancer. Infect Agent Cancer 2017;12:55.
Liu B, Wang Y, Melana SM, et al. Identification of a proviral structure in human breast cancer. Cancer Res 2001;61(4):1754-9.
Vadlapatla RK, Pal D, Vadlapudl AD et al. Ritonavir: A powerful boosting agent for overcoming drug resistance in cancer chemotherapy. Cancer Sci Ther 2014,6:11.
Mazzanti CM, Lessi F, Armogida I, et al. Human saliva as route of inter-human infection for mouse mammary tumor virus. Oncotarget 2015;6(21):18355-63.
Melana SM, Holland JF, Pogo BG. Search for mouse mammary tumor virus-like env sequences in cancer and normal breast from the same individuals. Clin Cancer Res 2001;7(2):283-4.
Melana SM, Nepomnaschy I, Sakalian M, et al. Characterization of viral particles isolated from primary cultures of human breast cancer cells. Cancer Res 2007;67(18):8960-5.
Moore R, Dixon M, Smith R, Peters G, Dickson C. Complete nucleotide sequence of a milk-transmitted mouse mammary tumor virus: two frameshift suppression events are required for translation of gag and pol. J Virol 1987;61(2):480-90.
Nartey T, Mazzanti CM, Melana S, et al. Mouse mammary tumor-like virus (MMTV) is present in human breast tissue before development of virally associated breast cancer. Infect Agent Cancer 2017;12:1.
Nartey T, Moran H, Marin T, et al. Human mammary tumor virus (HMTV) sequences in human milk. Infect Agent Cancer 2014;9:20.
Ohba K, Ichiyama K, Yajima M, et al. In vivo and in vitro studies suggest a possible involvement of HPV infection in the early stage of breast carcinogenesis via APOBEC3B induction. Plos One 2014;9(5):e97787.
Corresponding PCT International Search Report and Written Opinion dated Nov. 19, 2020.
Drugs.com; Ritonavir Dosage; Publication online Mar. 28, 2019.
Lytvyak et al.; World Journal of Gastroenterology; Combination Antiretroviral Studies for Patients with Primary Biliary Cirrhosis; Jan. 7, 2016.
Drugs.com; Atazanavir Dosage; Apr. 15, 2019.
Braitbard, et al.; A new immunization and treatment strategy for mouse mammary tumor virus; Feb. 26, 2016.
Canadian Office Action dated Feb. 2, 2023 from corresponding Canadian Application No. 3145293.

* cited by examiner

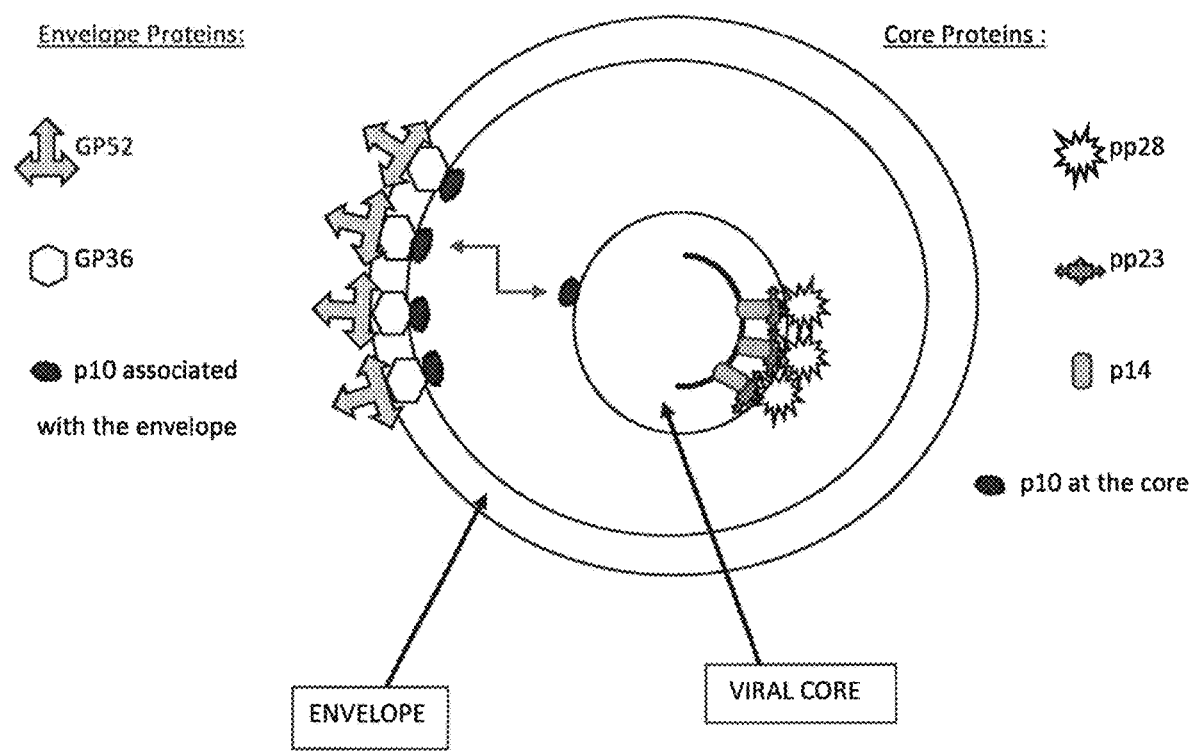

MAMMARY TUMOR VIRUS SUPPRESSION

APPLICATION CROSS-REFERENCE

The instant application is a Continuation-in-Part of U.S. application Ser. No. 16/460,295 filed on 2 Jul. 2019, the entirety of which is incorporated by reference. The application also relates to PCT/US19/40361 filed on 2 Jul. 2019, the entirety of which is incorporated by reference. The instant application further relates to U.S. Provisional Patent Application Ser. No. 62/934,858 filed on 13 Nov. 2019, the entirety of which is incorporated by reference.

SUBMISSION OF SEQUENCE LISTING ON ASCII TEXT FILE

The instant application contains a Sequence Listing which has been submitted electronically in ASCII format and is hereby incorporated by reference in its entirety. Said ASCII file, created on 2 Jul. 2020, is named 1133-0002-1-CIP-SL.txt and is 7,384 bytes in size. The content of the ASCII text file incorporated herein by reference is a computer readable form (CRF) of three sequences:
  SEQ. 1 Illustrates an example Pr75gag polyprotein sequence.
  SEQ. 2 Illustrates an example transitional protein p10 sequence.
  SEQ. 3 Illustrates an artificial cDNA sequence encoding a modified p10 transitional protein.

BACKGROUND

Technical Field

Embodiments of the invention generally fall into the category of suppression of viral replication. In some embodiments a protease inhibitor is used to control viral replication to prevent recurrence or metastasis in patients with invasive viral-mediated cancers. In other embodiments the protease inhibitor is combined with a cDNA produced peptide.

Discussion of Art

The etiology of breast cancer is likely multi-factorial. Genetics are known to play a role (BRCA for example), as do diet, and hormones (Dudley, 2016). The mammary tumor virus (MTV) is found across a broad range of species, mammals in particular. The virus is implicated as a general tumor-forming virus, suggesting that it may well be a wide-ranging zoonotic tumor virus with deep penetration throughout our shared environment.

The Mouse Mammary Tumor Virus (MMTV) was first described by Bittner in 1936, in the context of its being an exogenous infectious agent that was transmitted from mother mouse to baby mouse through breastmilk. Weiss later categorized it as a B type retrovirus, comparable to HIV, but carried in far smaller concentrations (1996). As a B type retrovirus, MTV belongs to a group globally recognized as oncogenic. As such, it acts through insertional mutagenesis, ultimately producing a tumor in its target tissue.

MMTV strains vary according to species of mouse, which itself varies by geography and historical custom. The observance of the parallel trends in MMTV expression and human breast cancer led to a probable associative link between the two. Areas that have higher concentrations of rodents and have had them for a longer period of time show increased virulence and increased rates of cancer. In fact, the incidence and manifestation of breast cancer in humans can be directly correlated to the species of mouse endemic to a given area. Regions where mouse populations are generally low, like East Asia, have lower overall breast cancer rates, and those populations have tumors that exhibit very low virus positivity (Khan, 2008; San, 2017). The most virulent strains of MMTV lie in the Middle East, an area with a higher rodent population and where breast cancer onset and severity are more pronounced than elsewhere (Chouchane, 2013). In the United States and Mexico, where mice are ubiquitous, tumor samples test positive for the MMTV virus (Cedro, 2014) and can be linked to the "house mouse," *Mus domesticus* (Stewart, 2000).

A hormonally-activated and regulated retrovirus, the genetic code of MTV is fully deciphered for variants found in some mammalian species. The genetic code of the deciphered variants share a common genetic architecture with many other retroviruses with major expression groups comprising: long terminal repeats (LTR); group antigen polyproteins (GAG); reverse transcriptases and polymerases (POL); and, envelope proteins (ENV). FIG. 1 provides an illustration of this generalized architectural structure for MTV. The proteins that compose the GAG group generally form the viral core structure, RNA genome binding proteins, and are the major proteins comprising the nucleoprotein core. The GAG group may also encode viral matrix, capsid, and nucleoproteins. The POL reverse transcriptase is the essential enzyme that carries out the reverse transcription process that takes the viral RNA genome to a double-stranded DNA pre-integrated form. The ENV group encodes for host cell transmembrane and surface-receptor subunits, and regulatory subunits found on the endoplasmic reticulum of the host cell in addition to the proteins that form the viral envelope.

The MMTV virus, while endemic to mice, appears to be acquired within the species itself. An antigenic component, the gp52 envelope protein can reliably be found in the blood and reproductive organs of infected mice (Arthur, 1978), as can antibodies to envelope proteins such as gp52. The virus is passed through breast milk, urine, feces, and/or saliva, and it travels liberally until it finds hormone-dependent tissues to infect, with breast being the preferred target. Once inside a cell, the virus randomly inserts into a series of integration sites (Faschinger, 2008), ultimately meeting an oncogene and producing the necessary frameshift to cause a cancer-producing mutation (Moore, 1987).

Due to the apparent connection between MMTV exposure and breast cancer in mice, coupled with the above mouse population-human breast cancer prevalence observations, many efforts have been made to find a human correlate to the virus, the Human Mammary Tumor Virus (HMTV), and its subsequent role in breast cancer in women. A human corollary found to be 85-95% homologous to MMTV was described by Melana and Holland in 2001. This HMTV was identified in human breast cancer specimens, first through identification of homologous MMTV envelope proteins (Wang, 1995) and later with the discovery of proviral units specific to human subjects (Liu, 2001).

While the prevalence of HMTV in breast cancer tissue has varied widely across studies, there is evidence that it is consistently well-represented in certain types of cancers, namely ductal carcinoma in situ (DCIS; Mazzanti, 2011). Even in subjects with significant disease, the virus may be somewhat elusive, owing to the fact that it is present in low concentrations (Bindra, 2007), and serves as a relatively remote precursor to oncogenesis (Nartey, 2017). Viral acquisition predates tumor formation by one to eleven years (Lawson, 2017), with the virus itself possibly becoming less virulent after initial mutagenesis. Ultimately, viral particles can be detected in tumor tissue and breast milk (Nartey, 2014), demonstrating a predilection for that organ system. The affinity for breast tissue includes male subjects as well, in whom particles have been isolated from benign cases of gynecomastia (Ford, 2004).

HMTV shares homology with MMTV in both form and action and the two share similar genetic sequences. As used herein the term "homolog" and its derivatives are, unless specified with a percentage, used as commonly understood by practitioners in the field of biochemistry in that proteins sharing similar behavioral properties, structural motifs, or performing similar functions with conserved domains across a family are said to be "homologous" to each other. Likewise, sequence data for DNA or RNA may be more or less "homologous" in that shared identities across species are said to be "homologous." When used as a percentage, homologous is interpreted to mean a comparison of sequences (DNA, RNA, peptide) with sequences above a certain percentage similarity or bearing certain conserved structural motifs at key positions said to be "homologous" with other sequences.

Human breast tumors demonstrate evidence of envelope protein units, as well as equivalent RNA segments known to originate from MMTV (Axel, 1962). The HMTV virus inserts similarly into the genome at random sites, ultimately inciting comparable mutations by activating various oncogenes (Callahan, 2012). Representatives of the envelope protein can be localized to the host cell membrane, but are more prominent in cellular cytoplasm (Tomana, 1981).

In general, transcription processes read through an MTV genome and mRNA is polyadenylated and processed using signals in transcribed regions from the 3' LTR at the end of the transcribed RNA. The full-length message can be spliced to lead to production of envelope proteins (or other proteins depending upon retroviral class). Unspliced full-length mRNA can give rise to GAG-POL precursor polyproteins. Alternatively, GAG and POL proteins, and other MTV proteins, or protein subunits may first arise from translated mRNA polypeptide precursor molecules. Multiple precursors are possible and may contain multiple proteins or protein subunits. A viral protease cleaves the precursor into multiple subunits with varying functions. An ENV protein complex, for example, may be translated from mRNA segments into multiple precursors which are then cleaved by endogenous proteases to yield multiple subunits that assemble into a mature surface glycoprotein.

Translated proteins assemble a retroviral particle at the host cell surface. Full-length genomic unspliced mRNA (containing a packaging signal termed Psi) is bound by GAG-derived proteins and incorporated into the budding particle. As a B-type retrovirus the general structure of a mature MTV particle is characterized by prominent surface protein "spikes" and a dense acentric nucleocapsid.

The discovery of Human Endogenous Retroviruses (HERV) DNA sequences embedded in the genome led to the hypothesis that many retroviruses, or genetic elements derived from retroviruses, are now endogenous to humans; the result of many generations of people being repeatedly exposed to the agents and eventually integrating them into their DNA. The HERV equivalent to MTV has been found in human subjects (Salmon, 2014). Some researchers hypothesize that HMTV is purely endogenous, and that efforts at curtailing its oncogenic potential should be directed at genetic manipulation rather than immunization against an exogenous entity (Yang, et al., 1987).

MTV behaves in a fashion more consistent as an exogenous particle (Ford, 2004; Melana, 2007). The fact that the virus is acquired up to ten years prior to disease onset in view of the fact that the mean age of onset of breast cancer is over 50 leads the argument for an endogenous factor to fall short. Furthermore, the measured immunogenicity against MTV is consistent with that of an acquired infection, and is maximal during disease latency (Black, 1976).

In the setting of MTV and its probable role in breast cancer, there is strong evidence in support of a combinatorial effect of MTV with multiple oncogenic viruses acting in conjunction and potentiating each other during tumorigenesis (Corbex, 2014; Glenn, 2012; Lawson, 2018; Al Moustafa, 2016). Taken as a whole, the data on MTV suggests that there are in fact endogenous and exogenous versions of the virus, many with little clinical relevance to immediate disease. It is also probable that the HERVs previously described represent remnants of prior integrations, and that newer incidences of MTV infection ultimately lead to cancer onset.

The retrovirus replication cycle is characterized by conversion of the single-strand RNA viral genome into double-strand proviral DNA by the multiple enzymatic activities of the virus-associated reverse transcriptase. Integration of MMTV proviral DNA into the genome of host cells is required for the expression of viral proteins. In both infected mouse mammary glands as wells as heterologous cells MMTV proviral DNA is integrated into a large number of apparently random sites. Integration of MMTV proviruses containing transcriptionally active long terminal repeats (LTR) near some cellular genes (proto-oncogenes) involved with oncogenesis can result in over-expression of these genes resulting in cellular transformation and clonal expansion of tumor cells. Thus, the long latency of MMTV-induced carcinogenesis is explained in part by the necessity for proviruses to integrate into oncogenetic sites.

Efforts at measuring MTV antibodies have had varying success. Antibodies to some envelope proteins have been isolated, although sparingly, as they seem to wane with disease progression as previously mentioned. The MTV virus itself also appears to have evolved mechanisms that blunt the host response to infection (Dudley, 2016). Previous diagnostic tests for MTV in humans have been limited to localizing the envelope protein in the host, as opposed to finding the more prevalent and longer lasting intracellular elements. (Holland, 1995) A further example of a similar attempt may be found in Garry (U.S. Pat. No. 6,670,466) the teachings of which are hereby incorporated by reference in their entirety.

While mice are ubiquitous and are known to be present in both homes and food storage facilities, MTV appears to require more intimate contact for effective transmission. Various efforts to detect MTV in other species have shown that correlates are found in primates, feline and canine species, in addition to the well-known mouse model (Szabo, 2005). Cross-species transmission is possible, as evidenced by the acquisition of MMTV in lab personnel who performed frequent handling of infected mice (Dion, 1986).

MTV appears to require repeated and frequent exposure for effective transmission. To that end, domesticated pets have become the prime targets for study, and the prime suspects as vectors. MTV particles are found in the non-cancer cells of house pets, with sequences similar to those of infected mice (Hsu, 2010). Pet-human interaction being frequent and extensive, studies then proceeded to identify the most common mode of transmission between them. Given that MTV has been detected in various body fluids, saliva was next to be evaluated for its virulent potential.

In 2015, Mazzanti identified MMTV particles in human saliva, suggesting that to be one mode of transmission between humans. Extrapolating from that data, it is likely that the house pets in whom MTV variants are found also have the virus present in their saliva, and pet saliva itself is ubiquitous in human homes. Dog ownership in particular has been isolated as an independent risk factor for breast cancer in women (Laumbacher, 2006), a fact anecdotally replicated on a daily basis in oncologic surgery practices in the United States.

Finally, given the above putative associations between MTV and cancer there have been past attempts at creating an MTV vaccine. However, the prior attempts at generating an MTV vaccine have used ENV proteins or protein parts (e.g., Garry) and failed to raise the required immune response. Thus, there is a need for an MTV vaccine capable of inducing immunity in humans and in human-associated animals. Further, as the oncogenic properties of exogenous MTV are only recently recognized, there is a need to develop treatments effective at lowering viral particle load and/or activity.

BRIEF SUMMARY OF THE INVENTION

An embodiment of the invention is a method of reducing breast cancer recurrence via prevention of MTV transcription in breast tissue via administration of a protease inhibitor. Other compositions contemplated as part of various embodiments of the instant invention provide a means for stabilizing or reducing the amount of virus present in a human or other animal.

In another embodiment of the invention a patient is first tested for the presence of MTV. Upon discovery of MTV the patient is then administered an antiretroviral medication. In some embodiments the antiretroviral medication is a protease inhibitor. In other embodiments the antiretroviral treatment may be one or more selected from the group of: nucleoside analogue reverse transcriptase inhibitors, nucleotide analogue reverse transcriptase inhibitors, non-nucleoside reverse transcriptase inhibitors.

In still other embodiments the antiretroviral medication, such as a protease inhibitor, is administered to a subject at a first dosage level, corresponding to a treatment level, and then altered to a second or more dosage level corresponding to a maintenance level. In still other embodiments the test for MTV presence is an antibody titer test. In still other embodiments the antibody test relies on antibodies raised in response to at least one of: GP52, a transition protein, and p14. In still other embodiments the transition protein is p10.

In another embodiment a patient with a breast cancer diagnosis, or a patient with breast cancer risk factors is treated with an antiretroviral medication. In still other embodiments this treatment is combined with the administration of MTV transition proteins or transition protein peptides.

In still another embodiment a cDNA encoding an MTV transition protein is provided. The protein may be myristoylated and, likewise, the cDNA may encode for this modification. Also provided are cDNA molecules encoding MTV transition protein peptide chains of greater or lesser length with or without a myristol. The transition protein or transition protein peptide chains may then be incorporated as part of an MTV vaccine or treatment regimen administered to a patient for control of MTV particle count or viral activity.

BRIEF DESCRIPTION OF THE DRAWINGS

Features and advantages of embodiments of the present invention will become apparent on reading the detailed description below with reference to the drawings, which are illustrative but non-limiting, wherein:

FIG. 1 Illustrates the general generic genomic structure of a generic MTV.

FIG. 2 Illustrates a schematic representation of Pr75gag cleavage products.

FIG. 3 Illustrates a schematic of an MTV virus.

DETAILED DESCRIPTION OF THE INVENTION

Although described herein as singular genetic elements, each class of ENV, GAG, POL, and LTR, may encode for multiple proteins, subunits, glycosylation sites, or signaling factors. Vaccines also include a variety of ingredients besides classifying antigens and can include: stabilizers, adjuvants, antibiotics, and preservatives. Those skilled in the art of pharmaceutical preparation are able to select appropriate additional ingredients in the course of standard practice. In this instance the term "vaccine" is used as ordinarily understood and may also contain a secondary descriptor describing the antigenic component eliciting the desired immune response along with the associated ingredients tailored to the desired effect. It is further understood that a vaccine may be all or part of a "pharmaceutical preparation" as herein defined and may incorporate a combination of natural and synthetic components. In certain instances it is recognized in the art that bringing together two natural components, a viral piece and an adjuvant, give rise to a composition with properties greater than the sum of its parts. (i.e., conferring a greater immune response, providing stabilization of antigens, etc.) It is those enhanced, non-naturally occurring properties to which the term "vaccine" further contemplates.

There are many types of vaccines, categorized by the antigen used in their preparation. Their formulations affect how they are used, how they are stored, and how they are administered. There are at least four main types of vaccine: Live Attenuated Virus ("LAV"), Inactivated (killed antigen), Subunit (purified antigen), and Toxoid (inactivated toxins). Vaccines may be monovalent or polyvalent. A monovalent vaccine contains a single strain of a single antigen (e.g. Measles vaccine), whereas a polyvalent vaccine contains two or more strains/serotypes of the same antigen (e.g. OPV). Some of the above antigens may be combined in a single injection that can prevent different diseases or that protect against multiple strains of infectious agents causing the same disease (e.g. combination vaccine DPT combining diphtheria, pertussis, and tetanus antigens). Thus, combination vaccines can be useful to overcome the logistic constraints of multiple injections and accommodate for a patient's fear of needles and pain. As used in this application, the term "polyvalent vaccine" refers to multiple antigen types that may derive from a single or multiple disease vectors whereas a "combination vaccine" refers to a vaccine with multiple antigens targeting at least two or more diseases. Thus, a "polyvalent vaccine" may have multiple antigens but only provide immunity to a single disease whereas a "combination vaccine" may contain a single type of antigen from two or more disease vectors and give rise to an immunity for those two or more diseases. Also, as used herein the term "patient" reflects a human or animal subject to whom a medical treatment is provided either for modification of a disease state or as a prophylactic preventative of disease.

Available since the 1950s, live attenuated vaccines (LAV) are derived from disease-causing pathogens (virus or bacteria) that have been weakened under laboratory conditions. They will grow in a vaccinated individual, but because they are weak, they will cause no or very mild disease. Inactivated vaccines are made from microorganisms (viruses, bacteria, other) that have been killed through physical or chemical processes. These killed organisms cannot cause disease.

Subunit vaccines, like inactivated whole-cell vaccines do not contain live components of the pathogen. They differ from inactivated whole-cell vaccines, by containing only the antigenic parts of the pathogen. Protein based subunit vaccines present an antigen to the immune system without viral particles, using a specific, isolated protein of the pathogen. Some bacteria when infecting humans are often protected by a polysaccharide (sugar) capsule that helps the organism evade the human defense systems especially in infants and young children. Polysaccharide vaccines create a response against the molecules in the pathogen's capsule. Conjugate subunit vaccines also create a response against the molecules in the pathogen's capsule. In comparison to plain polysaccharide vaccines, they benefit from a technology that binds the polysaccharide to a carrier protein that can induce a long-term protective response.

Toxoid vaccines are based on the toxin produced by certain bacteria (e.g. tetanus or diphtheria). The toxin invades the bloodstream and is largely responsible for the symptoms of the disease. A protein-based toxin is rendered harmless (toxoid) and used as the antigen in the vaccine to elicit immunity. To increase the immune response, the toxoid is often adsorbed to aluminum or calcium salts, which serve as adjuvants.

Thus, a live vaccine can have different associated ingredients than a subunit-based vaccine. Both are vaccines and raise an immune response in patients but with different antigens. Or, in the alternative, two live vaccines may have the same antigen but varied ingredients (e.g., in response to administration requirements). Or, in other embodiments, the vaccine may have the same antigen (e.g., an ENV protein or protein subunit) that is derived from one or more sources (e.g., an ENV protein from a human and one from a cat). In other embodiments, two or more antigenic components may be combined to increase immune system response greater than an individual antigen alone (e.g., an ENV protein combined with a protein precursor). Additionally, antigens for MTV may be combined with other antigens for other diseases into a mono or polyvalent combination vaccine.

The term "antigens" and derivatives are defined as the components typically derived from the structure of disease-causing organisms, which are recognized as "foreign" by the immune system and trigger a protective immune response to the vaccine. Importantly, the antigen component does not have to be made by the disease-causing organism in order to be used. For example, viral proteins or protein precursors may be manufactured and purified using bacterial, fungal, cell free, or other vector-based systems in bulk and then purified for use in a vaccine serum or other pharmaceutical preparation.

Vaccines may be administered through multiple routes at least including: intramuscular injection, subcutaneous injection, intradermal injection, orally, or through intranasal sprays. It is understood that each route of administration may require its own mix of antigens and associated ingredients.

In this application synthetic proteins and derivatives are prefixed with an "syn" such as synMTV or synENV, synPOL, etc. to differentiate from naturally occurring versions. For example, an synENV protein may be derived from a genetic sequence identical to or modified from (e.g., introns removed, different starter code and reading frame, different promoters etc.) a naturally occurring sequence but produced in an alternative system of protein expression (e.g., in yeast or *E. coli*, etc.). Likewise, the amino acid sequences, and underlying genetics, for each protein may vary across viral sub-species found in different mammalian species. synProteins or synProtein subunits (such as those produced by a protein cleavage process, those produced by restriction processes, or those produced by artificial amino-acid peptide chain construction, amino acid printing, or other artificial systems or protein or protein product expression) may be derived in whole or in part from single or multiple viral sub-types (e.g., human sequence synProtein combined with a homologous canine synProtein to form a polyvalent vaccine protective against both HMTV and canine MTV virus particles).

In an example embodiment, an engineered vaccine is created by synthesizing and purifying an EP3-p14-p10 peptide chain. The peptides, in haptan formulation, are coupled to keyhole limpet hemocyanin (KLH) and extensively dialyzed. Moles of conjugated peptide/mole of KLH are determined by amino acid analysis and range between 700 and 1,000. Positive and negative controls consist of gp52, purified from C3H-MMTV and a scrambled peptide sequence coupled to KLH respectively. Still other embodiments may employ different carrier proteins including at least: *Concholepas concholepas* hemocyanin, bovine serum albumin (BSA), cationized BSA, or ovalbumin, and any other carrier proteins. In still another embodiment, multiple antigens, for instance from other viral-mediated cancers or tumor-associated antigens, or for other diseases which may be vaccinated against, may also be attached to one or more carrier proteins and combined to form a polyvalent combination vaccine. In practice, the vaccine is administered to patients either as a prophylactic preventative or, in the case of patients with a known MTV exposure as a means of inducing or bolstering an immune response.

The MTV envelope (ENV) class of proteins is known to have conserved domain elements across variants of the virus detected across multiple species. In particular, the ENV proteins may comprise those that are signaling peptides, those that are specific to the outer membrane of the virus particle, those specific to the endoplasmic reticulum, and those that are trans-membrane anchors. The polymerase (POL) protein class may comprise both a polymerase and/or a reverse transcriptase and an associated signaling factor. The group antigen (GAG) proteins form the viral core structure, RNA genome binding proteins, and are the major proteins comprising the nucleoprotein core particle. The POL and GAG group proteins are likewise thought to have conserved cross-species elements.

Without subscribing or limiting to any specific theory or practice, variants within and between the above genetic motifs may account for viral traits such as specificity, genetic integration location, surface protein structures, species specificity, etc. Thus, by altering combinations one may target a vaccine to protect against an MTV exposure in various species. This may be accomplished by either deriving viral proteins from the target species of interest or utilizing synProteins or synProtein subunits derived from species-specific sequence data. A target species may be one whose MTV viral protein sequences, although homologous, differ enough from the primary MTV antigen in a vaccine that a separate antigen is required to raise or enhance an immune response either in the species of interest or to increase an immune response, for example in a human, in reaction to an exposure of an MTV variant from the target species. For example, a human MTV vaccine with a transition protein may include additional MTV polypeptide antigens whose sequences are derived from human companion species such as a dog, cat, ferret, etc. Thus, while the vaccine may also possibly be administered to the human-companion animal to reduce viral load in the animal (and hence exposure to the human), the additional MTV component also strengthens the immune response of the human to the target species variant of MTV.

Accordingly, another embodiment of the invention comprises an MTV vaccine derived from attenuated or inactivated MTV particles derived from either single or multiple species. Other embodiment vaccines are derived from synProteins and synProtein subunits of the ENV, POL, and GAG protein classes. An additional embodiment is composed of synProteins and/or synProtein subunits derived from cross-species conserved sequences. For example, some portions of the sequence of the gp52 ENV protein are known to be conserved across MTV variants. Thus, a synProtein subunit based on the conserved sequence could be used in a vaccine to induce immunity to MTV in multiple species, including human-associated animals such as dogs, cats, and other human-companion animals or increase the immune response in a human to MTV variants derived from the animals.

As used herein the term "derived from" is used as ordinarily understood: that is, a sequence (DNA, RNA, or peptide) may be found across multiple species with minor variations while still preserving a high sequence identity. Thus, while one can recognize, for example, MTV protein p10 in general, it is the unique mutations, sometimes in the form of single nucleotide polymorphisms (SNPs), that allow one skilled in the art to identify a p10 sequence from a human, compared to another mammal, such as a mouse. In another sense, in addition to identifying sequence sources, "derived from" encompasses and contemplates the source of raw stock materials, binders, supports, carrier proteins, etc. (e.g., KLH is derived from a protein found in keyhole limpets even if commercial embodiments of it are produced in alternative production systems, such as vector-based expression systems).

In still another example embodiment, a purified MTV virus from one or multiple species is combined with 1.2× $10^{-2}$M formalin for a concentration of 1:3,000 formaldehyde. It is then incubated in the dark at 4° C. for 5 days (or room temperature for 72 h) and stored at 4° C. It is diluted to contain 50 ng protein µl$^-$ and emulsified with an equal volume of complete Freund's adjuvant (CFA) or other pharmaceutically acceptable adjuvant. The preparation is then stored at −70° C. until used. In some embodiments the above serum is combined with one or more additional vaccine sera to form polyvalent, compound, or compound polyvalent vaccines targeted at one or more additional diseases. The resulting pharmaceutical preparation is then administered to a patient for either prophylactic or treatment purposes.

In another example embodiment, MTV virus particles from one or multiple species may be subjected to fragmentation processes designed to break apart the virus into multiple protein and protein pieces (e.g., sonication, vibration, freeze-fracture, etc.). MTV proteins and/or protein subunits may then be collected, purified, and fixed in a vaccine preparation. Particular preparations may include purified ENV, POL, or GAG proteins or protein subunits. In a further embodiment the purified proteins may include p10, p14, and gp52.

As briefly outlined above, RNA viruses in many families and genera express their genomes in ways which involve the synthesis and subsequent cleavage of polypeptide chains known as precursor polyproteins. This stratagem allows the activation of subsets of proteins with different biochemical functions from the same precursor polyprotein. Although the virus-encoded enzymes responsible for processing the polyproteins are structurally diverse, they are all highly specific for their substrates. The resulting processing cascade is a tightly controlled process, which in several cases involves the action of protein cofactors to modulate the activity of the proteinase. Antigens for use in a vaccine can derive from protein precursors.

Figure 2:

In general, MTV proteins are synthesized with at least two major precursor polyproteins, for MMTV this includes: gPr75env containing gp52 and gp36; and, Pr75gag containing p27, pp20, p14, and p10. SEQ. ID: 01 illustrates an example sequence for a Pr75gag precursor polyprotein, the cleavage products of which are schematically illustrated in FIG. 2. Shown in FIG. 2, for example, p14 is a signal peptide subunit of an ENV protein. p14 can also function in both oncogenic and an anti-oncogenic capacity depending on its phosphorylation status. Also shown in FIG. 2, p10 is part of the same polyprotein precursor as p14 and is also found as a cleavage product thereof. SEQ. ID: 02 illustrates an example sequence of a p10 protein. Those skilled in the art readily recognize that the above sequences are conserved across multiple species without significant deviation. It is a routine skill to find and identify homologous sequences in multiple species and, indeed, homologous sequences for p10 are found in humans, mice, cats, and canines.

As illustrated in FIG. 3, p10 initially starts at the viral core and then transitions to the envelope membrane of the virus. This core-to-envelope transition protein is believed to be a representative member of a larger class of core-to-envelope proteins. As used herein the term "transition protein" describes a protein, that moves between the viral core and the viral envelope (i.e., from core to envelope or envelope to core). In an embodiment the transition protein may start at the viral core and then move to the viral envelope. The transition protein may thus remain at the underside of the envelope, may transition through the envelope to the exterior, or may span across the viral envelope. A transition protein may also be a protein subunit that forms part of a larger protein. It may be directly produced from viral mRNA, viral DNA, cDNA, or be the result of cleavage from a precursor polyprotein either naturally produced in vivo or synthetically produced (e.g., in a vector-based production system). Thus, an embodiment of the invention includes an MTV transition protein either alone or in combination with further MTV proteins. An MTV transition protein may also be synthetically generated and combined with other antigens or formed as part of a polyvalent, or compound polyvalent vaccine targeting one or multiple diseases and administered to a patient either prophylactically or as a modifier of a disease state.

Thus, in another embodiment an MTV vaccine preparation containing one or more precursor proteins either derived from polyprotein cleavage products or directly created using alternative protein expression means. In particular polyprotein cleavage products, p10, p14, and, alone or in combination with each other, may be combined with at least one ENV, GAG, or POL protein or protein derivative. Still other embodiments may include gp52, gp36, and p28 proteins. These may then be combined with an MTV transition protein, such as p10.

In addition to MTV, other virus species, termed oncoviruses, are possible sources of oncogenesis; these can include at least: Epstein-Barr Virus (EBV) (Ballard, 2015; Lebreque, 1995), human immunodeficiency virus (HIV), human papilloma virus (HPV), herpes simplex virus (HSV), and bovine leukemia virus (BLV) (Baltzell, 2018; Buehring, 2017). It is believed, without subscribing or limiting to a particular theory, and as briefly outlined above, that viruses often work together to potentiate each other and to cause disease in general. Oncogenic viruses in particular can work together to cause disease. Specifically, RNA viruses tend to be unstable but highly virulent, DNA viruses tend to be stable but not as aggressive. DNA and RNA viruses can work together, each building upon the strengths of the other to increase pathogenicity. It is believed that many viruses like HPV and HSV can make other viruses more virulent, and that certain combinations are particularly effective at inducing oncogenesis in patients.

Further, RNA viruses and DNA viruses may have a complimentary effect wherein the high replication and mutation rates of RNA viruses may be stabilized by the less mutagenic DNA viruses, allowing for optimal adaptability without loss of control. The highly active MTV RNA virus, as discussed above, replicates quickly and randomly inserts into the genome, often producing no effect. Genomically-integrated MTV sequences can be found with little to no clinical relevance, and these are often misinterpreted as being endogenous. Once stabilized and directed by a DNA partner, the usually erratic agent can now target its source more effectively and remain consistent long enough to provoke oncogenesis. This is one possible mechanism for HPV/MTV synergy in cancer formation.

Accordingly, embodiments of the invention are directed towards the treatment of breast, prostate, and other viral-mediated cancers or other synergestic diseases in humans and other animals. In some embodiments a protective immunity is formed in patients as a result of vaccination with MTV or synMTV either in whole, in part, or in combinations as part of live, attenuated, or subunit vaccines along with antigenic components of other oncogenic virus particles such as at least: EBV, HIV, HPV, HSV, and BLV. In other embodiments, an MTV vaccine is administered to a patient diagnosed with a viral-mediated cancer with the effect of reducing the malignancy, spread, or recurrence of the viral-mediated cancer.

As noted above, the incidence of breast cancer in humans is increased in areas with increased mouse populations. Also, as above, humans with pets may also experience an increased incidence of breast cancer. Any of the above described vaccines may be altered to target a particular species. For example, a monovalent vaccine targeting a rabbit may use an MTV protein or protein particles purified from rabbit-specific MTV. Likewise, a human targeting vaccine may use ENV protein purified from HMTV strains found in humans. Or, in the alternative, a synthetically derived synProteins or hybrids may be created based upon a target species MTV genetic sequence. In alternative embodiments MTV derived POL or GAG proteins or protein subunits may be used. In an alternative embodiment the vaccine may be composed of peptides derived from one or more conserved sequences found across target species, for example, human, mouse, canine, feline, bovine, and other human-companion animals. Thus, a multi-species MTV vaccine may be created. Additionally, animal vaccination may be used in tandem with human vaccination to decrease the overall incidence of breast cancer and other viral mediated cancers in a human population by decreasing human exposure to MTV transmitted via animals.

Another embodiment of the invention is a polyvalent vaccine comprised of multiple MTV antigen components. In certain embodiments the components may be a mixture of natural and synthetically derived components, for example, a synthetic synENV mixed with a naturally occurring ENV or POL. The polyvalent vaccine may further contain precursor cleavage products such as p10, mp10 (which is a p10 peptide in myristoylated form with or without subsequent conformational changes), or p14. These may further be combined with one or more transition proteins and may be further combined into a combination vaccine or suitable pharmaceutical preparation.

An embodiment of the invention is a vaccine comprising an MTV transition protein administered to a patient. In some embodiments the MTV transition protein is p10. In some embodiments the vaccine further comprises additional antigens to form a combination vaccine. In still other embodiments the vaccine contains at least one additional MTV component. In some embodiments the one additional MTV component is derived from at least one of: gp52, p14, syngp52, MTV polymerase, synMTV polymerase, MTV transcriptase, synMTV transcriptase, MTV surface, synMTV surface, MTV transmembrane anchoring, synMTV transmembrane anchoring, MTV-associated polysaccharide, and synMTV-associated polysaccharide. In another embodiment there is at least a second MTV component derived from a target species different from the first MTV component. In still other embodiments the vaccine may further contain MTV derived ENV and POL. In still other embodiments at least one of the ENV, POL and MTV transition proteins is synthetically derived. In another embodiment the vaccine may also contain a polysaccharide. In still other embodiments the vaccine may comprise additional antigens to form a combination polyvalent vaccine. In certain embodiments the additional antigens are derived from at least one of: an oncovirus, and a tumor-associated antigen.

In some embodiments the vaccine contains MTV polypeptides coupled to a carrier protein. In certain embodiments the MTV polyeptides are EP3, p14, and an MTV transition protein; and, the carrier protein is KLH. In further embodiments the MTV transition protein is p10 as exemplified in SEQ. ID: 2 or a homologous sequence with at least 90% identity thereof. In certain other embodiments the carrier protein is at least one selected from the group of KLH, *Concholepas concholepas* hemocyanin, BSA, Cationized BSA, and Ovalbumin. In certain other embodiments the vaccine also contains additional antigens to form a compound polyvalent vaccine.

Thus, by way of non-limiting example, an MTV vaccine comprising EP3, p10, and p14 bound to KLH along with any additional pharmaceutically acceptable compounds may be prophylactically provided to an MTV naïve patient. In response to the vaccine the patient immune system mounts a response resulting in long term immunity from subsequent MTV exposure.

Other embodiments of the current invention provide for pharmaceutical compositions comprising MTV DNA, RNA and/or proteins described herein. These compositions may further comprise a pharmaceutically acceptable excipient, carrier, or diluent and do not contain any biologically harmful substances. The pharmaceutical compositions of the present invention may be formulated by one having ordinary skill in the art. Suitable pharmaceutical formulations are described in Remington's Pharmaceutical Sciences which is a standard reference text in the field which is herein incorporated by reference.

The pharmaceutical compositions may further comprise coloring or stabilizing agents, osmotic agents, antibacterial agents, or any other substances as long as such substances do not interfere with the function of the composition. The pharmaceutical compositions of the instant invention, can, for example, be formulated as a solution, suspension, or emulsion in association with a pharmaceutically acceptable parenteral vehicle. Examples of such vehicles are water, saline, Ringer's solution, dextrose solution, and 5% human albumen. Liposomes may also be used. The vehicle may contain additives that maintain isotonicity (e.g., sodium chloride or mannitol) and chemical stability (e.g., buffers and preservatives). It should be appreciated that endotoxin contamination should be kept at a safe level, for example, less than 0.5 ng mg$^{-1}$ protein. Moreover, for human administration, preparations should meet sterility, pyrogenicity, general safety and purity standards as required by the United States Food and Drug Administration Office of Biological Standards. The formulations may be sterilized by commonly used techniques such as filtration.

The phrase "pharmaceutically acceptable" refers to substances and compositions which do not produce an adverse, allergic, or otherwise untoward reaction when administered to an animal, or a human, as appropriate. A substance which caused or produced any of these adverse effects would be classified as "biologically harmful' within the scope of the present invention. Pharmaceutically acceptable substances and compositions include, but are not limited to solvents, dispersion media, coatings, antibacterial and antifungal agents, isotonic and absorption delaying agents. Except where incompatible with the invention the use of any conventional ingredient is contemplated. Furthermore, supplementary active ingredients which serve some other pharmacologically expedient purpose can also be incorporated into the instant compositions without departing from the broader scope of the instant invention.

Another embodiment of the invention is a method of treating MTV where an MTV vaccine with an MTV transition protein is provided and administered to a patient. In some embodiments the vaccine is administered in conjunction with additional vaccines or other medical treatments as below described. In still other embodiments the vaccine is administered to at least one of a human, and a human associated animal. The vaccine may be administered as a preventative prophylactic to induce an immune response in a naïve host resulting in immunity to subsequent MTV exposure, or may be administered to an exposed patient for the purposes of bolstering an immune response to an extant viral presence. In such instances, either viral particle count or other measures of viral presence and/or activity are decreased as a result of vaccine administration.

Protease inhibitors are an example of one class of retroviral medications. As described above, MTV reproduction relies upon production and then cleavage of precursor proteins. In general, a protease inhibitor prevents cleavage of the viral precursor protein by inhibiting the action of the viral protease responsible for the cleavage. Thus, viral loads in a host are decreased as the virus fails to replicate. Accordingly, an embodiment of the invention results in the decrease of MTV loads in a patient accomplished through the administration of protease inhibitors. Example protease inhibitors can include at least one of: atazanavir (Reyataz), darunavir (Prezista), fosamprenavir (Lexiva), indinavir (Crixivan), lopinavir/ritonavir (Kaletra), nelfinavir (Viracept), ritonavir (Norvir), saquinavir (Invirase), tipranavir (Aptivus), atazanavir/cobicistat (Evotaz), and, darunavir/cobicistat (Prezcobix) either alone or in combination with another protease inhibitor. A method of treating a patient exposed to MTV may include: determining through an antibody or other test patient exposure status to MTV; then administering either a treatment dose or a maintenance dose of a protease inhibitor. In another embodiment, the protease inhibitor may be administered in conjunction with an MTV vaccine of the like described above thus decreasing viral load in a patient. In other embodiments, the patient may, instead, have a cancer diagnosis, or present other cancer-associated risk factors, without measurement of MTV levels or detection of MTV presence. The diagnosed cancer may, for example, be breast cancer or prostate cancer, or another viral-mediated cancer. In still other embodiments the patient may be analyzed for one or more risk factors (e.g., familial history, work history, past cancer status, etc.). Patients deemed above a given risk threshold may be deemed "high risk" and provided with antiretroviral medications as above described.

A treatment dosage is used as commonly understood in the art as one calculated to immediately or gradually (the terms "immediately" or "gradually" understood to be qualitative and relative, not quantitative) reduce a high viral load in a patient. In certain embodiments, patient exposure to MTV is determined through the use of an antibody titer test. In particular, the antibody test may detect antibodies to at least one of: gp52, p10, and p14. A maintenance dosage, as commonly understood, is one calculated to sustain a low or non-detectable limit of viral particles. An initial treatment dosage may be decreased to a maintenance dosage. Likewise, a treatment dosage with one or more primary protease inhibitors may be effected and then replaced with a maintenance dosage of one or more secondary protease inhibitors. In similar fashion, maintenance dosages may be increased or decreased as demanded by either viral load measurements or treatment protocols.

By way of non-limiting example, ritonavir may be provided to a patient as a maintenance dosage in the range of 50-440 mg per day, or atazanvir at 300-400 mg per day. In combination, ritonavir may be used with a range of 50-400 mg per day combined with another protease inhibitor at 100-400 mg per day. Protease inhibitors may also be used in combination with chemotherapy drugs to first treat a cancer (e.g., breast cancer or other viral-mediated cancer) and then used singly to prevent cancer recurrence. As used herein, dosage ranges explicitly contemplate every integer or part dosage amount (e.g., 1, 1.1, 1.2, 1.3, etc.) within the range including the initial and end amounts within the range. It is recognized that while ranges may list start and end points manufacturing tolerances and the like may result in products above or below range within a specified tolerance.

A method of treating MTV exposure in a patient can comprise: determining the MTV exposure status of a patient; and, administering a protease inhibitor to a patient with MTV exposure. In a further embodiment, the protease inhibitor may be administered in conjunction with an MTV vaccine. In still another embodiment the MTV vaccine may contain a transition protein. In still another embodiment the transition protein may be p10.

The method described above may further be modified wherein the administration of the protease inhibitor is performed at a first treatment dosage and a second maintenance dosage. In some embodiments an MTV vaccine may be administered during the treatment dosage administration. In still other embodiments, the MTV vaccine may be administered when switching to a maintenance dosage. In some embodiments the maintenance dosage is in the range of 50-200 mg of medication per day.

The method described above may be further modified wherein the protease inhibitor is administered in conjunction with chemotherapeutic agents in a cancerous patient. The protease inhibitor dosage may be altered from a treatment dosage to a maintenance dosage or switched to a second protease inhibitor at a maintenance dosage upon either cessation of chemotherapy treatments or remission of cancer. In certain cases, the cancer may be breast cancer, prostate cancer or another viral-mediated cancer.

In some embodiments of the method described above the protease inhibitor is at least one of: atazanavir (Reyataz), darunavir (Prezista), fosamprenavir (Lexiva), indinavir (Crixivan), lopinavir/ritonavir (Kaletra), nelfinavir (Viracept), ritonavir (Norvir), saquinavir (Invirase), tipranavir (Aptivus), atazanavir/cobicistat (Evotaz), and, darunavir/cobicistat (Prezcobix). In still other embodiments ritonavir is combined with at least one more protease inhibitor. In some embodiments the ritonavir is combined with at least one of: atazanavir (Reyataz), darunavir (Prezista), fosamprenavir (Lexiva), indinavir (Crixivan), lopinavir/ritonavir (Kaletra), nelfinavir (Viracept), ritonavir (Norvir), saquinavir (Invirase), tipranavir (Aptivus), atazanavir/cobicistat (Evotaz), and, darunavir/cobicistat (Prezcobix).

In some embodiments of the method above the protease inhibitor is ritonavier provided as a maintenance dosage in the range of 50-440 mg per day, or atazanvir at 300-400 mg per day.

In some embodiments, ritonavir may be used with a range of 50-400 mg per day and combined with another protease inhibitor at 100-400 mg per day.

In another embodiment of the invention a patient is first tested for the presence of MTV. Upon discovery of evidence of MTV exposure, the patient is then administered an antiretroviral medication. In some embodiments the antiretroviral medication is a protease inhibitor. In still other embodiments the protease inhibitor is administered at a first dosage level, corresponding to a treatment level, and then altered to a second or more dosage level corresponding to a maintenance level. In still other embodiments the test for MTV is an antibody test. In still other embodiments the antibody test relies on antibodies raised in response to at least one of: GP52, a transition protein, and p14. In still other embodiments the transition protein is p10.

For example, a patient with MTV exposure may first be treated with ritonavir at a dosage of 70 mg per day, concomitantly an MTV vaccine with an MTV transition protein is administered. The net effect results in an overall decrease in patient MTV viral particle loading and/or measured activity. Upon lowering of the MTV viral particle loading and/or measured activity, a second maintenance dosage of antiretroviral medications may be started. The net effect of the combined treatment is to halt the spread of an MTV viral-mediated cancer resulting in remission and/or the prevention of relapse.

In another embodiment, a patient with a cancer diagnosis is administered an antiretroviral medication. In some embodiments the antiretroviral medication is a protease inhibitor. In some embodiments the cancer diagnosis is for breast cancer. In still other embodiments the cancer diagnosis is for a viral-mediated cancer. In still other embodiments the protease inhibitor is administered at a first dosage level, corresponding to a treatment level, and then altered to a second or more dosage level corresponding to a second or more maintenance level. The method described above may further be modified wherein the administration of the protease inhibitor is performed at a first treatment dosage and a second maintenance dosage. In some embodiments an MTV vaccine may be administered during the treatment dosage administration. In still other embodiments, the MTV vaccine may be administered when switching to a maintenance dosage. In some embodiments the maintenance dosage is in the range of 50-200 mg of medication per day. In still other embodiments the MTV vaccine contains an MTV transition protein.

The effective dose and method of administration of a particular embodiment of the instant invention may vary based on the individual patient and stage of any present diseases (e.g., breast cancer, HIV, other co-morbidities), as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by an individual physician in view of a patient to be treated. Dosage and administration are adjusted to provide sufficient levels of embodiments of the instant invention to maintain the desired effect (e.g., elimination or reduction of MTV particles or activity in a host). Additional factors that may be taken into account include the severity of any disease state, age, weight, and gender of the patient; diet, time and frequency of the administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks or more. Depending on half-life and clearance rate of the particular formulation, the pharmaceutical compositions of the instant invention may be administered once, twice, three, four, five, six, seven, eight, nine, ten or more times per day.

Normal dosage amounts may vary from approximately 1 to 100,000 micrograms, up to a total dose of about 10 grams, depending upon the route of administration. Desirable dosages include 250 µg, 500 µg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5 g, 6 g, 7 g, 8 g, 9 g, and 10 g.

More specifically, the dosage of peptide agents described herein is one that provides sufficient peptide agent to attain a desirable effect, including stimulation of the immune system to produce antibodies, and/or disruption of the production of MTV viral particles. Accordingly, the dose of the peptide agent preferably produces a tissue or blood concentration of both about 1 to 800 µM. Preferable doses produces a tissue or blood concentration of greater than about 10 µM to about 500 µM. Preferable doses are, for example, the amount of peptide required to achieve a tissue or blood concentration or both of 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 110 µM, 120 µM, 130 µM, 140 µM, 150 µM, 160 µM, 170 µM, 180 µM, 190 µM, 200 µM, 220 µM, 240 µM, 250 µM, 260 µM, 280 µM, 300 µM, 320 µM, 340 µM, 360 µM, 380 µM, 400 µM, 420 µM, 440 µM, 460 µM, 480 µM, and 500 µM. Although doses that produce a tissue concentration greater than 800 µM are not necessarily preferred, they are envisioned and can be used with some embodiments of the present invention. A constant infusion of embodiments of the invention can be provided so as to maintain a stable concentration of the therapeutic agents (e.g., modified MTV peptides, MTV transition proteins, additional proteins or peptides co-administered, and other medicines such as retrovirals as herein described).

Protein N-myristoylation is a cotranslational lipidic modification specific to the alpha-amino group of an N-terminal glycine residue of many eukaryotic and viral proteins. The ubiquitous eukaryotic enzyme, N-myristoyltransferase (NMT), catalyzes the myristoylation process. Precisely, attachment of a myristoyl group increases specific protein-protein interactions leading to subcellular localization of myristoylated proteins with their signaling partners. The birth of the field of myristoylation, a little over three decades ago, has led to the understanding of the significance of protein myristoylation in regulating cellular signaling pathways in several biological processes especially in carcinogenesis and, more recently, immune function.

Typically, the myristate moiety participates in protein subcellular localization by facilitating protein-membrane interactions as well as protein-protein interactions. Myristoylated proteins are crucial components of a wide variety of functions, which include many signaling pathways, oncogenesis or viral replication. The attachment of myristic acid to the N-terminus is catalyzed by the ubiquitous eukaryotic enzyme, N-myristoyltransferase (NMT); a prosurvival protein, which uses myristoyl-coenzyme A (CoA) as a substrate. Although myristoylation typically occurs cotranslationally on newly synthesized polypeptides following cleavage of the initiator methionine by methionine aminopeptidase, there is also evidence that NMT-mediated posttranslational modification of proteins occurs after proteolytic cleavage of an N-terminal glycine residue.

Myristic acid is a hydrophobic moiety, and as the cell microenvironment is hydrophilic, the myristoylated protein is inserted into hydrophobic regions within the cell namely on: lipid rafts, the plasma membrane, endoplasmic reticulum (ER), Golgi apparatus, nuclear membrane, and mitochondria. Thus, depending on the subcellular localization of the myristoylated protein, it can regulate diverse cellular functions. Myristoylated proteins are adapted to performing biological functions in signal transduction, cellular transformation, and oncogenesis. Myristic acid is not an abundant fatty acid, it accounts for less than 1% of the total fatty acid in the cell, introducing another form of regulation.

Without subscribing to or limiting to a particular theory or practice, myristoylated proteins and/or peptide chains derived therefrom may further enhance the antigenic properties when used in combinations with further adjuvants. Hence, modified proteins and/or protein peptide chains may be myristoylated and used alone or in pharmaceutical compositions as described above to trigger or enhance an immune response leading to decreased or eliminated viral particle loads and/or activity. In particular, myristoylation may provide a means of anchoring an antigenic protein or peptide chain into cell membranes or carrier molecules enhancing their presentment to the immune system for an increased immune response resulting in either lasting immunity in a patient or decreased viral loading and/or activity.

There are often protein purification tags applied to peptide sequences to ease purification of synthetic proteins from a production system. For example, in immobilized metal ion chromatography (IMAC), a his-tag, or polyhistidine tag, is a string of histidine residues added at either the N or C terminus of a recombinant protein. There can be from four to ten residues in a string, although commonly there are six histidine residues a hexahistidine tag. Some recombinant proteins are engineered to have two or more hexahistidine tags.

In IMAC, transition metal ions are immobilized on a resin matrix using a chelating agent such as iminodiacetic acid. The most common ion for his-tag purification of a recombinant protein is Ni2+, though Co2+, Cu2+, and Zn2+ are also used. The his-tag has a high affinity for these metal ions and binds strongly to the IMAC column. Most other proteins in the lysate will not bind to the resin or bind only weakly. The use of a his-tag and IMAC can often provide relatively pure recombinant protein directly from a crude lysate.

Imidazole competes with the his-tag for binding to the metal-charged resin and thus is used for elution of the protein from an IMAC column. Typically, a low concentration of imidazole is added to both binding and wash buffers to interfere with the weak binding of other proteins and to elute any proteins that weakly bind. His-tagged protein is then eluted with a higher concentration of imidazole. Proteins with different numbers of poly histidine tags elute differently from nickel-affinity resin. For example, proteins with a single hexahistidine tag may elute from a Ni-NTA column at 75 mM of imidazole whereas proteins with two hexahistadine tags may require 100 mM imidazole solution to elute from the same column.

Some example alternatives to His-tag purification commonly include: HQ-tag (alternating histidine and glutamine); HN-tag (alternating histidine and asparagine), HAT-tag which is a peptide tag. Practitioners of ordinary skill in the art will readily recognize that any suitable purification tag may be added to embodiments without departing from the scope of the invention.

Embodiments of the present invention provide for isolated cDNA, DNA, RNA, and polypeptides derived from viral transition proteins including those from HMTV and MMTV and human associated animals. Accordingly an embodiment of the present invention provides for a recombinant cDNA plasmid (a vector) which comprises MTV DNA at least 90% identical to SEQ ID No: 2. In some embodiments, the plasmid vector further comprises a heterologous promoter operably linked to the MTV sequence (i.e., joined in the proper reading frame so as to be capable of producing functional MTV RNA and/or protein in vivo and in vitro). In one aspect of this embodiment of the invention the vector, which comprises the MTV DNA, is capable of episomal replication or chromosomal integration in at least one of the following cell types: bacterial cells, yeast cells, insect cells, avian cells, and mammalian cells (this list of cell types is representative and should not be considered exhaustive). In still other embodiments, the MTV DNA is modified to include an N-terminal glycine residue capable of myristoylation. In still other embodiments an artificial cDNA encoding a transition protein sequence, such as that of SEQ ID No: 2, comprises: a promoter sequence; a first position methionine; a second position glycine; a portion of or all of the sequence of a transition protein; one or more purification tags; a stop codon; and, the appropriate promoters and coding sequences for one or more additional genes for co-expression. In some embodiments the additional genes encoded include: myristoyl-CoA:protein N-myristoyltransferase (NMT). In certain other expression systems, the additional genes may further include methionine aminopeptidase. Those of ordinary skill in the art without undue experimentation will recognize the need for sequence modifications adapted to their unique vector and/or protein expression systems without departing from the scope of the invention. Thus, those of skill in the art will recognize that one of the end products of this process is a myristoylated transition protein peptide chain. In some embodiments the myristoylated transition protein peptide chain is 90% or more homologous with the peptide encoded by SEQ ID No: 2. In still other embodiments the myristoylated transition protein peptide chain is 10 or more contiguous amino acids as found in SEQ ID No: 2 or an acceptably homologous sequence.

An example of an artificial cDNA sequence containing MTV protein p10 is provided at SEQ ID No: 3. In this example, the p10 sequence is altered to include an additional N-terminal glycine residue after an added initial methionine residue in order to enable myristoylation of the produced peptide. The sequence further includes a hexahistidine tag sequence with a 3× Gly linker. The sequence is left open to reflect the possibility of adding additional sequences. Those of ordinary skill in the art will be able to select appropriate promoter sequences for creation of final vector forms. In DNA/cDNA sequences example promotion sequences can include TATA box/Pribnow box sequences.

In certain embodiments the cDNA is incorporated into a vector, such as a plasmid, which is then subsequently expressed in the expression systems noted above for peptide/protein production. The peptide chains, with or without myristoylation are then purified and then incorporated into an acceptable pharmaceutical preparation as above disclosed. In certain embodiments a "linker" sequence (e.g., gly-gly-gly or gly-ser-gly) may be incorporated between the peptide chain and the his-tag. In subsequent purification steps the his-tag may then be removed.

In an example embodiment a purified transition protein peptide chain alone or in combination with a myristol group is combined into a pharmaceutical preparation as above described and administered to a patient with confirmed MTV exposure or, displaying MTV risk factors, or with a concomitant cancer diagnosis (viral-mediated or otherwise) with a resulting decrease in MTV viral load or activity.

Finally, the written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The pharmacologically active compounds of this invention can be processed in accordance with conventional methods of galenic pharmacy to produce medicinal agents for administration to patients (e.g., mammals including humans). The peptides with, or without, modification can be incorporated into a pharmaceutical composition. Further, the manufacture of pharmaceuticals or therapeutic agents that deliver the peptides or a nucleic acid sequence encoding a peptide by several routes is an embodiment. By way of non-limiting example, DNA, RNA, and viral vectors having sequences that encoding a transition protein peptide with antigenic properties are contemplated. Nucleic acids encoding a desired transition protein peptide can be administered alone or in combination with a transition protein peptide resulting in lowered MTV viral particle counts or lowered measurements of MTV virus activity either via direct action or enhanced immune response.

As used herein the term "sequence" explicitly contemplates DNA, cDNA, RNA and resulting peptide chains encoded thereby in both sense and antisense directions. To know one is to know the others via the standard rules of complementarity and codon encoding as exemplified in standardized DNA, RNA, and amino acid codon tables.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A method, comprising:

administering an antiretroviral medication to a patient the antiretroviral medication being a protease inhibitor; and administering a pharmaceutical composition containing an MTV protein of SEQ ID: 02 and an adjuvant in conjunction with the antiretroviral medication.

2. The method of claim 1 further comprising:

administering the antiretroviral medication at a first treatment dosage and at least a second maintenance dosage; and administering the pharmaceutical composition during the treatment dosage administration.

3. The method of claim 1 further comprising:

administering the antiretroviral medication at a first treatment dosage and at least a second maintenance dosage; and administering the pharmaceutical composition when switching to the maintenance dosage.

4. The method of claim 3 further comprising:

wherein the maintenance dosage is in the range of 50-200 mg of medication per day.

5. The method of claim 1 further comprising:

administering the antiretroviral medication in conjunction with chemotherapeutic agents; and, altering the antiretroviral medication dosage from a treatment dosage to a maintenance dosage.

6. The method of claim 5 further comprising:

switching to a second antiretroviral medication at a maintenance dosage upon either cessation of chemotherapy treatments or remission of cancer.

7. The method of claim 1 further comprising:

wherein the protease inhibitor is at least one selected from the group of: atazanavir, darunavir, fosamprenavir, indinavir, lopinavir/ritonavir, nelfinavir, ritonavir, saquinavir, tipranavir, atazanavir/cobicistat, and, darunavir/cobicistat.

8. The method of claim 7 further comprising:

combining the ritonavir with at least one more protease inhibitor.

9. The method of claim 8, wherein:

the at least one more protease inhibitor is at least one selected from the group of: atazanavir, darunavir, fosamprenavir, indinavir, lopinavir/ritonavir, nelfinavir, ritonavir at a different dosage, saquinavir, tipranavir, atazanavir/cobicistat, and, darunavir/cobicistat.

10. The method of claim 6 wherein the second antiretroviral medication is at least one selected from the group of: ritonavir at a maintenance dosage in the range of 50-440 mg per day, and atazanavir at a maintenance dosage in the range of 300-400 mg per day.

11. The method of claim 8 wherein the ritonavir is dosed at a range of 50-400 mg per day and combined with another protease inhibitor at 100-400 mg per day.

12. A method, comprising:

testing a patient for the presence of MTV;

confirming the presence of MTV in the patient;

administering a protease inhibitor to the patient; and administering a pharmaceutical preparation containing an MTV protein of SEQID:02 and an adjuvant in conjunction with the protease inhibitor.

13. The method of claim 12 further comprising:

administering the protease inhibitor at a first dosage rate, corresponding to a treatment level; and, altering at least one additional dosage rate corresponding to at least a first maintenance level.

14. The method of claim 12 further comprising:

utilizing an antibody test to test the patient for the presence of MTV.

15. The method of claim 14 further comprising:

wherein the antibody test relies on antibodies raised in response to at least one selected from the group of: gp52, a transition protein of SEQ ID:02, and p14.

16. A method, comprising:

administering to a person with MTV exposure a pharmaceutical composition containing a transition protein of SEQID:02 and an adjuvant; and administering an antiretroviral medication.

* * * * *

SEQUENCE LISTING

<160> NUMBER OF SEQ ID NOS: 3

<210> SEQ ID NO 1
<211> LENGTH: 590
<212> TYPE: PRT
<213> ORGANISM: Mammary Tumor Virus

<400> SEQUENCE: 1

Gly Val Ser Gly Ser Lys Gly Gln Lys Leu Phe Val Ser Val Leu Gln
1               5                   10                  15

Arg Leu Leu Ser Glu Arg Gly Leu His Val Lys Glu Ser Ser Ala Ile

```
            20                  25                  30
Glu Phe Tyr Gln Phe Leu Ile Lys Val Ser Pro Trp Phe Pro Glu Glu
         35                  40                  45

Gly Gly Leu Asn Leu Gln Asp Trp Lys Arg Val Gly Arg Glu Met Lys
     50                  55                  60

Arg Tyr Ala Ala Glu His Gly Thr Asp Ser Ile Pro Lys Gln Ala Tyr
 65                  70                  75                  80

Pro Ile Trp Leu Gln Leu Arg Glu Ile Leu Thr Glu Gln Ser Asp Leu
                 85                  90                  95

Val Leu Leu Ser Ala Glu Ala Lys Ser Val Thr Glu Glu Leu Glu
             100                 105                 110

Glu Gly Leu Thr Gly Leu Leu Ser Thr Ser Gln Glu Lys Thr Tyr
         115                 120                 125

Gly Thr Arg Gly Thr Ala Tyr Ala Glu Ile Asp Thr Glu Val Asp Lys
             130                 135                 140

Leu Ser Glu His Ile Tyr Asp Glu Pro Tyr Glu Glu Lys Glu Lys Ala
145                 150                 155                 160

Asp Lys Asn Glu Glu Lys Asp His Val Arg Lys Ile Lys Lys Val Val
                 165                 170                 175

Gln Arg Lys Glu Asn Ser Glu Gly Lys Arg Lys Glu Lys Asp Ser Lys
             180                 185                 190

Ala Phe Leu Ala Thr Asp Trp Asn Asp Asp Leu Ser Pro Glu Asp
             195                 200                 205

Trp Asp Asp Leu Glu Glu Gln Ala Ala His Tyr His Asp Asp Glu
     210                 215                 220

Leu Ile Leu Pro Val Lys Arg Lys Val Lys Lys Pro Gln Ala
225                 230                 235                 240

Leu Arg Arg Lys Pro Leu Pro Pro Val Gly Phe Ala Gly Ala Met Ala
                 245                 250                 255

Glu Ala Arg Glu Lys Gly Asp Leu Thr Phe Thr Phe Pro Val Val Phe
             260                 265                 270

Met Gly Glu Ser Asp Glu Asp Thr Pro Val Trp Glu Pro Leu Pro
     275                 280                 285

Leu Lys Thr Leu Lys Glu Leu Gln Ser Ala Val Arg Thr Met Gly Pro
     290                 295                 300

Ser Ala Pro Tyr Thr Leu Gln Val Val Asp Met Val Ala Ser Gln Trp
305                 310                 315                 320

Leu Thr Pro Ser Asp Trp His Gln Thr Ala Arg Ala Thr Leu Ser Pro
                 325                 330                 335

Gly Asp Tyr Val Leu Trp Arg Thr Glu Tyr Glu Glu Lys Ser Lys Glu
             340                 345                 350

Met Val Gln Lys Ala Ala Gly Lys Arg Lys Gly Lys Val Ser Leu Asp
             355                 360                 365

Met Leu Leu Gly Thr Gly Gln Phe Leu Ser Pro Ser Ser Gln Ile Lys
     370                 375                 380

Leu Ser Lys Asp Val Leu Lys Asp Val Thr Thr Asn Ala Val Leu Ala
385                 390                 395                 400

Trp Arg Ala Ile Pro Pro Gly Val Lys Lys Thr Val Leu Ala Gly
                 405                 410                 415

Leu Lys Gln Gly Asn Glu Glu Ser Tyr Glu Thr Phe Ile Ser Arg Leu
             420                 425                 430

Glu Glu Ala Val Tyr Arg Met Met Pro Arg Gly Glu Gly Ser Asp Ile
             435                 440                 445
```

Leu Ile Lys Gln Leu Ala Trp Glu Asn Ala Asn Ser Leu Cys Gln Asp
            450                 455                 460

Leu Ile Arg Pro Ile Arg Lys Thr Gly Thr Ile Gln Asp Tyr Ile Arg
465                 470                 475                 480

Ala Cys Leu Asp Ala Ser Pro Ala Val Val Gln Gly Met Ala Tyr Ala
                485                 490                 495

Ala Ala Met Arg Gly Gln Lys Tyr Ser Thr Phe Val Lys Gln Thr Tyr
                500                 505                 510

Gly Gly Gly Lys Gly Gly Gln Gly Ala Glu Gly Pro Val Cys Phe Ser
                515                 520                 525

Cys Gly Lys Thr Gly His Ile Arg Lys Asp Cys Lys Asp Glu Lys Gly
            530                 535                 540

Ser Lys Arg Ala Pro Pro Gly Leu Cys Pro Arg Cys Lys Lys Gly Tyr
545                 550                 555                 560

His Trp Lys Ser Glu Cys Lys Ser Lys Phe Asp Lys Asp Gly Asn Pro
                565                 570                 575

Leu Pro Pro Leu Glu Thr Asn Ala Glu Asn Ser Lys Asn Leu
                580                 585                 590

<210> SEQ ID NO 2
<211> LENGTH: 98
<212> TYPE: PRT
<213> ORGANISM: Mammary Tumor Virus

<400> SEQUENCE: 2

Gly Val Ser Gly Ser Lys Gly Gln Lys Leu Phe Val Ser Val Leu Gln
1               5                   10                  15

Arg Leu Leu Ser Glu Arg Gly Leu His Val Lys Glu Ser Ser Ala Ile
                20                  25                  30

Glu Phe Tyr Gln Phe Leu Ile Lys Val Ser Pro Trp Phe Pro Glu Glu
            35                  40                  45

Gly Gly Leu Asn Leu Gln Asp Trp Lys Arg Val Gly Arg Glu Met Lys
        50                  55                  60

Arg Tyr Ala Ala Glu His Gly Thr Asp Ser Ile Pro Lys Gln Ala Tyr
65              70                  75                  80

Pro Ile Trp Leu Gln Leu Arg Glu Ile Leu Thr Glu Gln Ser Asp Leu
                85                  90                  95

Val Leu

<210> SEQ ID NO 3
<211> LENGTH: 109
<212> TYPE: PRT
<213> ORGANISM: Artificial Sequence
<220> FEATURE:
<223> OTHER INFORMATION: Product of the human mind.

<400> SEQUENCE: 3

Met Gly Gly Val Ser Gly Ser Lys Gly Gln Lys Leu Phe Val Ser Val
1               5                   10                  15

Leu Gln Arg Leu Leu Ser Glu Arg Gly Leu His Val Lys Glu Ser Ser
                20                  25                  30

Ala Ile Glu Phe Tyr Gln Phe Leu Ile Lys Val Ser Pro Trp Phe Pro
            35                  40                  45

Glu Glu Gly Gly Leu Asn Leu Gln Asp Trp Lys Arg Val Gly Arg Glu
        50                  55                  60

Met Lys Arg Tyr Ala Ala Glu His Gly Thr Asp Ser Ile Pro Lys Gln

-continued

```
65                  70                  75                  80

Ala Tyr Pro Ile Trp Leu Gln Leu Arg Glu Ile Leu Thr Glu Gln Ser
                85                  90                  95

Asp Leu Val Leu Gly Gly Gly His His His His His His
            100                 105
```